United States Patent [19]

Ashton et al.

[11] Patent Number: 4,933,350

[45] Date of Patent: Jun. 12, 1990

[54] PYRROLOISOQUINOLINES USEFUL AS HYPERCHOLESTEROLEMIC AND HYPERLIPOPROTIENIMIC AGENTS

[75] Inventors: Michael J. Ashton, Chelmsford; Donald I. Dron, Upminster; Garry Fenton, Brentwood; David J. Lythgoe, Gidea Park; Christopher G. Newton, Chelmsford; David Riddell, Billericay, all of England

[73] Assignee: May & Baker Limited, Dagenham, England

[21] Appl. No.: 230,038

[22] Filed: Aug. 9, 1988

[30] Foreign Application Priority Data

Aug. 11, 1987 [GB] United Kingdom ............ 8718980

[51] Int. Cl.$^5$ ............ A61K 31/47; C07D 471/04
[52] U.S. Cl. ............ 514/294; 546/94
[58] Field of Search ............ 546/94; 514/294

[56] References Cited

U.S. PATENT DOCUMENTS 3,019,232  1/1982  Sakorai et al. ............ 548/309

FOREIGN PATENT DOCUMENTS 7930887  4/1988  Australia .
0130069  of 0000  European Pat. Off. .
0150474  of 0000  European Pat. Off. .
3633840  4/1988  Fed. Rep. of Germany .
1261125  8/1988  Fed. Rep. of Germany .
1153670  of 0000  United Kingdom .

OTHER PUBLICATIONS

March, J., Advanced Organic Chemistry, 3rd ed. (1985), pp. 333–336, 348–349, 691–696, 809–811, 1057–1059.
Journal of Organic Chemistry, vol. 47, No. 1982.
Journal of Medicinal Chemistry, vol. 11, 1968.

Primary Examiner—Richard A. Schwartz
Assistant Examiner—Richard A. Sharpe
Attorney, Agent, or Firm—Stevens, Davis, Miller & Mosher

[57] ABSTRACT

Pyrrolo[2,1-a]isoquinoline derivatives of the formula:

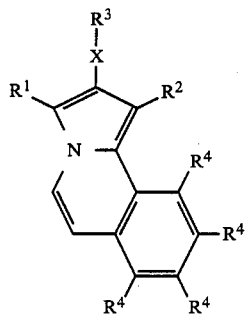

I wherein $R^1$ and $R^2$ each represent cycloalkyl or alkyl, alkenyl or alkynyl which may be halogen-substituted, or optionally substituted aryl or heteroaryl, X represents ethylene or vinylene, $R^3$ represents a group of the formula:

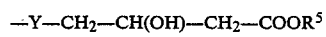

II wherein Y represents carbonyl or hydroxymethylene and $R^5$ represents hydrogen or optionally substituted alkyl, or $R^3$ represents a lactone ring, and the symbols $R^4$ represent hydrogen, halogen, optionally substituted alkyl, alkenyl or alkynyl, optionally substituted aryl or heteroaryl, or a group of the formula $R^6O-$, wherein $R^6$ represents alkyl, aryl or arylalkyl and pharmaceutical properties.

12 Claims, No Drawings

PYRROLOISOQUINOLINES USEFUL AS HYPERCHOLESTEROLEMIC AND HYPERLIPOPROTIENIMIC AGENTS

The present invention relates to new therapeutically useful pyrrolo[2,1-a]isoquinoline derivatives, to processes for their preparation, to pharmaceutical compositions containing them, and to their use as pharmaceuticals.

The pyrrolo[2,1-a]isoquinoline derivatives are the compounds of general formula I shown at the end of the present specification, wherein $R^1$ and $R^2$, which may be the same or, preferably, different, each represent a cycloalkyl group containing from 3 to 8 carbon atoms, or represent a straight- or branched-chain alkyl, alkenyl or alkynyl group containing up to 6 carbon atoms, which may be substituted by up to 3 halogen, preferably chlorine or fluorine, atoms, or an optionally substituted aryl, preferably phenyl, or heteroaryl group, X represents an ethylene or vinylene group, preferably a vinylene group in the E-configuration, $R^3$ represents a group of the general formula:

$$-Y-CH_2-CH(OH)-CH_2-COOR^5 \quad \text{II}$$

wherein Y represents a carbonyl or hydroxymethylene group and $R^5$ represents a hydrogen atom or an optionally substituted alkyl group containing up to 6 carbon atoms, or $R^3$ represents a lactone ring of general formula III shown at the end of the specification, and the symbols $R^4$ may be the same or different and each represents a hydrogen or halogen (i.e. fluorine, chlorine, bromine or iodine) atom or represents an optionally substituted straight- or branched-chain alkyl, alkenyl or alkynyl group containing up to 6 carbon atoms, or an optionally substituted aryl, preferably phenyl, or heteroaryl group, or a group of the formula $R^6O-$, wherein $R^6$ represents a straight or branched-chain alkyl group containing up to 6 carbon atoms, an aryl, e.g. phenyl, group, or an arylalkyl group containing 1 or 2 carbon atoms in the alkyl moiety, e.g. benzyl or phenethyl, and pharmaceutically acceptable salts thereof when $R^5$ represents a hydrogen atom, for example alkali metal, alkaline earth metal, ammonium and amine salts.

It is to be understood that, where in this specification reference is made to compounds of formula I, it is intended to refer also where the context so permits to their pharmaceutically acceptable salts.

Substituted alkyl, alkenyl or alkynyl groups within the definition of formula I unless otherwise specified preferably carry up to 3 substituents selected from halogen, preferably fluorine or chlorine, atoms and straight- or branched-chain alkoxy and alkylthio groups each containing up to 6 carbon atoms.

Substituted aryl and heteroaryl groups and moieties within the definition of formula I preferably carry one more substituents selected from halogen, preferably fluorine or chlorine, atoms, cycloalkyl and cycloalkenyl groups each containing from 4 to 8 carbon atoms, optionally substituted straight- or branched-chain alkyl, alkenyl or alkynyl groups each containing up to 6 carbon atoms, hydroxy groups, straight- or branched-chain alkoxy, alkylthio, alkylsulphinyl, alkylsulphonyl, alkoxycarbonyl and alkanoyl groups each containing up to 6 carbon atoms, and optionally substituted aryl, preferably phenyl, and heteroaryl groups.

As will be appreciated by those skilled in the art, the compounds of formula I may exist in various isomeric forms, for example diastereoisomeric forms, and all such forms and mixtures thereof are included within the scope of the invention. However, when $R^3$ represents a group of formula II and Y represents a hydroxymethylene group the erythro-form is the preferred form. When $R^3$ represents a group of formula III the preferred form has the hydroxy group attached to the lactone ring in the trans-configuration with respect to the rest of the molecule.

Preferably the lactone ring of formula III has the (4R,6S)-configuration.

The compounds of the general formula shown in FIG. I possess useful pharmacological properties, and some are useful as intermediates for the preparation of other therapeutically useful compounds, for example other compounds of formula I, for example as described later in this specification.

For example they lower the concentrations of cholesterol and of low density lipoproteins in the blood. Thus they are of utility in the prevention or treatment of hypercholesterolaemic and hyperlipoproteinaemic states, of atherosclerosis, and of associated conditions such as angina, myocardial infarction, cerebral vascular occlusion, arterial aneurism, peripheral vascular disease, recurrent pancreatitis and xanthomas.

Particularly important classes of compounds of formula I include those which exhibit one or more of the following features:

(i) one of $R^1$ and $R^2$, preferably $R^2$, represents an optionally substituted aryl or heteroaryl group, more particularly a substituted or unsubstituted phenyl group, for example a phenyl group substituted by a halogen, e.g. fluorine, atom, especially in the 4-position of the phenyl group, and the other one of $R^1$ and $R^2$, preferably $R^1$, represents a cycloalkyl group containing from 3 to 8 carbon atoms, or a straight- or branched-chain alkyl, alkenyl or alkynyl group containing up to 6 carbon atoms, which may be substituted by up to 3 halogen, preferably chlorine or fluorine, atoms, more particularly a straight- or branched-chain alkyl group, for example a methyl, ethyl or, preferably, isopropyl group;

(ii) Y represents a hydroxymethylene group;

(iii) $R^5$ represents a hydrogen atom or a methyl or ethyl group; and/or (iv) the symbols 4 all represent hydrogen atoms; the other symbols being as hereinbefore defined, and more especially, their pharmaceutically acceptable salts, particularly the alkali metal, e.g. sodium, salts.

Important compounds of formula I include the following:

| | |
|---|---|
| 3:2 mixture of erythro- and threo-diastereoisomers of methyl (E)-3,5-dihydroxy-7-(3-isopropyl-1-phenylpyrrolo[2,1-a]isoquinolin-2-yl)hept-6-enoate; | A |
| 2:1 mixture of erythro- and threo-diastereoisomers of sodium (E)-3,5-dihydroxy-7-(3-isopropyl-1-phenylpyrrolo[2,1-a]isoquinolin-2-yl)hept-6-enoate; | B |
| mixture of erythro- and threo-diastereoisomers of ethyl (E)-3,5-dihydroxy-7-(3-isopropyl-1-phenylpyrrolo[2,1-a]isoquinolin-2-yl)hept-6-enoate; | C |
| ethyl (E)-3-hydroxy-7-(3-isopropyl-1-phenylpyrrolo[2,1-a]isoquinolin-2-yl)-5-oxohept-6-enoate; | D |
| (E)-3-hydroxy-7-(3-isopropyl-1-phenylpyrrolo[2,1-a]isoquinolin-2-yl)-5-oxohept-6-enoic acid; | E |
| 3,5-dihydroxy-7-(3-isopropyl-1-phenylpyrrolo[2,1-a]isoquinolin-2-yl)heptanoic acid; | F |
| 1:2 mixture of the cis- and trans-lactone ring | G |

-continued

| | |
|---|---|
| isomers of 4-hydroxy-6-[2-(3-isopropyl-1-phenylpyrrolo[2,1-a]isoquinolin-2-yl)ethyl]3,4,5,6-tetrahydro-2H-pyran-2-one; | |
| ethyl (E)-3,5-dihydroxy-7-(3-methyl-1-phenyl-pyrrolo[2,1-a]isoquinolin-2-yl)hept-6-enoate; | H |
| sodium (E)-3,5-dihydroxy-7-(3-methyl-1-phenyl-pyrrolo[2,1-a]isoquinolin-2-yl)hept-6-enoate; | I |
| ethyl (E)-3,5-dihydroxy-7-{(3-ethyl-1-(4-fluoro-phenyl)pyrrolo[2,1-a]isoquinolin-2-yl}hept-6-enoate; | J |
| sodium (E)-3,5-dihydroxy-7-{3-ethyl-1-(4-fluoro-phenyl)pyrrolo[2,1-a]isoquinolin-2-yl}hept-6-enoate; | K |
| 3:2 mixture of erythro- and threo-diastereoisomers of ethyl (E)-3,5-dihydroxy-7-{1-isopropyl-3-(4-fluorophenyl)pyrrolo[2,1-a]isoquinolin-2-yl}hept-6-enoate; | L |
| 3:2 mixture of erythro- and threo-diastereoisomers of sodium (E)-3,5-dihydroxy-7-{1-isopropyl-3-(4-fluorophenyl)pyrrolo[2,1-a] isoquinolin-2-yl}hept-6-enoate; | M |
| ethyl (E)-3,5-dihydroxy-7-{3-isopropyl-1-(4-fluoro-phenyl)pyrrolo[2,1-a]isoquinolin-2-yl}hept-6-enoate; | N |
| ethyl erythro-(E)-3,5-dihydroxy-7-{3-isopropyl-1-(4-fluorophenyl)pyrrolo-[2,1-a]-isoquinolin-2-yl}-hept-6-enoate; | NA |
| ethyl threo-(E)-3,5-dihydroxy-7-{3-isopropyl-1-(4-fluorophenyl)pyrrolo-[2,1-a]-isoquinolin-2-yl}-hept-6-enoate; | NB |
| 3:2 mixture of erythro- and threo-diastereoisomers of sodium (E)-3,5-dihydroxy-7-{3-isopropyl-1-(4-fluorophenyl)pyrrolo[2,1-a]isoquinolin-2-yl}-hept-6-enoate; | O |
| sodium erythro-(E)-3,5-dihydroxy-7-{3-isopropyl-1-(4-fluorophenyl)pyrrolo[2,1-a]isoquinolin-2-yl)}-hept-6-enoate; | OA |
| sodium threo-(E)-3,5-dihydroxy-7-{3-isopropyl-1-(4-fluorophenyl)pyrrolo[2,1-a]isoquinolin-2-yl}-hept-6-enoate; | OB |
| ethyl (E)-3-hydroxy-7-{(3-isopropyl-1-(4-fluoro-phenyl)pyrrolo[2,1-a]isoquinolin-2-yl}-5-oxohept-6-enoate; and | P |
| sodium (E)-3-hydroxy-7-{3-isopropyl-1-(4-fluoro-phenyl)pyrrolo[2,1-a]isoquinolin-2-yl}-5-oxohept-6-enoate. | Q |

The letters A to Q are allocated to the compounds for easy reference later in this specification.

Compound B is of particular importance, especially its erythro-component. In tests, the compounds of formula I show good results as competitive inhibitors of 3-hydroxy-3-methylglutaryl coenzyme A (HMG CoA) reductase and as a consequence are inhibitors of cholesterol biosynthesis. For example, in tests the compounds produced inhibition in rat hepatic microsomal HMG CoA reductase activity in vitro as shown in the following Table I. In the table the concentrations of the test compounds are expressed in micrograms/ml.

TABLE I

| Compound | Concentration | % Inhibition |
|---|---|---|
| B | 20.0 | 98 |
| | 6.4 | 91 |
| | 2.0 | 81 |
| | 1.6 | 72 |
| | 0.4 | 44 |
| | 0.2 | 43 |
| | 0.1 | 28 |
| | 0.025 | 16 |
| E | 20.0 | 90 |
| | 6.7 | 71 |
| | 2.2 | 50 |
| G | 20.0 | 44 |
| | 6.7 | 38 |
| H | 20.0 | 70 |
| | 6.66 | 54 |
| | 2.22 | 33 |
| | 0.74 | 22 |
| | 0.24 | 26 |
| I | 20.0 | 85 |
| | 6.66 | 68 |
| | 2.22 | 46 |
| | 0.74 | 35 |
| | 0.25 | 39 |
| | 0.082 | 44 |
| K | 6.66 | 95 |
| | 2.22 | 86 |
| | 0.74 | 68 |
| | 0.24 | 46 |
| | 0.082 | 33 |
| | 0.0274 | 27 |
| M | 20.0 | 98 |
| | 6.66 | 96 |
| | 2.22 | 90 |
| | 0.74 | 78 |
| | 0.22 | 65 |
| | 0.2 | 74 |
| | 0.066 | 69 |
| | 0.022 | 63 |
| | 0.0074 | 46 |
| | 0.0025 | 33 |
| N | 2.22 | 95 |
| | 0.74 | 87 |
| | 0.25 | 74 |
| | 0.082 | 61 |
| | 0.0274 | 55 |
| | 0.0091 | 44 |
| O | 20.0 | 99 |
| | 6.66 | 97 |
| | 2.22 | 92 |
| | 0.74 | 81 |
| | 0.24 | 69 |
| OA | 2.22 | 95 |
| | 0.74 | 87 |
| | 0.24 | 74 |
| | 0.082 | 63 |
| | 0.0274 | 51 |
| | 0.0091 | 43 |
| | 0.00304 | 37 |
| OB | 2.22 | 70 |
| | 0.74 | 53 |
| | 0.25 | 38 |
| | 0.082 | 29 |
| | 0.0274 | 21 |
| Q | 6.66 | 89 |
| | 2.22 | 70 |
| | 0.74 | 45 |
| | 0.24 | 22 |
| | 0.082 | 8 |

In in vivo tests in rats oral doses of compound B produced inhibition in cholesterol biosynthesis as shown in Table II.

In the table the doses are expressed in mg/kg animal body weight.

TABLE II

| Dose | % Inhibition |
|---|---|
| 10.0 | 91 |
| 3.33 | 77 |
| 1.11 | 67 |

Compounds of formula I and intermediates for their preparation may be prepared by the application or adaptation of known methods, for example methods similar to those described hereinafter in the following Examples and Reference Examples.

Optionally the reactions may be carried out in an inert atmosphere.

For example, according to a feature of the invention, compounds of formula I wherein $R^3$ represents a group of formula II, wherein Y represents a hydroxymethylene group and $R^5$ represents an optionally substituted alkyl group containing up to 6 carbon atoms, and $R^1$, $R^2$, $R^4$ and X are as hereinbefore defined, are prepared by the reduction of compounds of general formula IV shown at the end of the specification, wherein $R^1$, $R^2$, and X are as hereinbefore defined and $R^7$ represents a group of the general formula:

$$-CH(OH)-CH_2-CO-CH_2-COOR^8 \quad \text{V}$$

wherein $R^8$ represents an optionally substituted alkyl group containing up to 6 carbon atoms. The reduction may be carried out by means of sodium borohydride, preferably in a lower alkanol, e.g. methanol, and preferably below room temperature, e.g. at or near to 0° C.

According to a further feature of the invention, compounds of formula I wherein $R^3$ represents a group of general formula II wherein $R^5$ represents a hydrogen atom ($R^1$, $R^2$, $R^4$, X and Y being as hereinbefore defined), or a salt thereof, are prepared from the corresponding compounds wherein $R^5$ represents an optionally substituted alkyl group containing up to 6 carbon atoms by hydrolysis by known methods, for example by reaction with an aqueous solution of the corresponding base, e.g. an alkali metal hydroxide, to form the salt, e.g. an alkali metal salt, optionally followed by acidification, e.g. by treatment with acetic acid, to form the parent carboxylic acid.

According to a further feature of the invention, compounds of formula I wherein $R^3$ represents a group of formula II, wherein Y represents a carbonyl group and $R^5$ represents an optionally substituted alkyl group containing up to 6 carbon atoms, $R^1$, $R^2$, $R^4$ and X being as hereinbefore defined are prepared by the oxidation of the corresponding compounds wherein Y represents a hydroxymethylene group. The oxidation may be carried out by reaction with activated manganese dioxide, preferably at or near room temperature.

According to a further feature of the invention, compounds of formula I wherein X represents an ethylene group, $R^3$ represents a group of formula II and $R^5$ represents an optionally substituted alkyl group containing up to 6 carbon atoms, Y, $R^1$, $R^2$ and $R^4$ being as hereinbefore defined, are prepared from corresponding compounds wherein X represents a vinylene group, by catalytic hydrogenation. Suitable catalysts include those containing palladium, e.g. palladium on charcoal or on calcium carbonate, or mixtures thereof.

According to a further feature of the invention, compounds of formula I wherein $R^3$ represents a lactone ring of formula III, $R^1$, $R^2$, $R^4$ and X being as hereinbefore defined, are prepared by the cyclisation of the corresponding compounds wherein $R^3$ represents a group of formula II, wherein Y represents a hydroxymethylene group and $R^5$ represents a hydrogen atom. Sometimes the cyclisation occurs spontaneously but sometimes it is preferable to warm or to heat the starting material. Conveniently the heating is carried out in a solvent such as toluene at temperatures up to the boiling point.

Optionally the reaction is carried out in the presence of a trace of an acid, e.g. glacial acetic acid.

The pharmaceutically acceptable salts may be prepared from parent compounds of formula I by known methods, for example by reaction of compounds of formula I (wherein $R^3$ represents a group of formula II in which $R^5$ represents a hydrogen atom) and the appropriate base, e.g. an alkali metal hydroxide or carbonate, an alkaline earth metal oxide, ammonia or an amine, in a suitable solvent which is preferably water in the case of the preparation of alkali and alkaline earth metal salts and water or isopropanol in the case of amine salts.

As well as being useful in themselves as pharmaceutically useful compounds, salts of the compounds of formula I wherein $R^3$ represents a group of formula II wherein $R^5$ represents a hydrogen atom are useful for the purpose of purification of the parent acids of formula I, for example by exploitation of the solubility differences between the salts and the parent acids in water and in organic solvents, by techniques well known to those skilled in the art. The parent acids of formula I can be regenerated from their salts by known methods, for example by treatment with a mineral acid, e.g. dilute hydrochloric acid, or an organic acid, e.g. acetic acid.

As will be readily appreciated by those skilled in the art, the compounds of formula I, including their aforementioned isomers, may be separated by the application or adaptation of known methods. For example, diastereoisomeric forms may be separated by chromatography using selective adsorption from solution or from the vapour phase onto suitable adsorbents, and enantiomeric forms of compounds of formula I wherein $R^3$ represents a group of formula II in which $R^5$ represents a hydrogen atom may be separated by formation of salts with an optically active base, followed by separation of the obtained pair of diastereoisomers by, for example, fractional crystallisation from a suitable solvent system, followed by separate regeneration of the enantiomeric acids.

Compounds of the formula shown in Figure IV may be prepared by the application or adaptation of known methods, for example methods illustrated in the following Reference Examples.

By the term "known methods" as used in this specification is meant methods used heretofore or known in the literature.

For example, compounds of formula IV wherein X represents an ethylene group and $R^1$, $R^2$, $R^4$ and $R^7$ are as hereinbefore defined, may be prepared by the catalytic reduction of corresponding compounds wherein X represents a vinylene group, under conditions similar to those described hereinbefore for the preparation of compounds of formula I wherein X represents an ethylene group by catalytic reduction.

Compounds of formula IV, wherein $R^1$, $R^2$, $R^4$, $R^7$ and X are as hereinbefore defined, may be prepared from compounds of the general formula VI shown at the end of the specification, wherein $R^1$, $R^2$, $R^4$ and X are as hereinbefore defined, by reaction with a dianion of a compound of the general formula:

$$CH_3COCH_2COOR^8 \quad \text{VII}$$

wherein $R^8$ is as hereinbefore defined, generated in situ by treatment with two equivalents of strong base, for example sodium hydride and/or butyl lithium, in a suitable solvent such as tetrahydrofuran and at between $-50°$ C. and $0°$ C.

Compounds of formula VI, wherein $R^1$, $R^2$, $R^4$ and X are as hereinbefore defined, may be prepared by the oxidation of compounds of the general formula VIII shown at the end of the specification, wherein $R^1$, $R^2$, $R^4$ and X are as hereinbefore defined, under conditions similar to those described hereinbefore for the preparation of compounds of formula I wherein Y represents a carbonyl group by oxidation.

Compounds of formula VIII, wherein $R^1$, $R^2$, $R^4$ and X are as hereinbefore defined, may be prepared by the reduction of compounds of the general formula IX shown at the end of the specification, wherein $R^1$, $R^2$, $R^4$ and X are as hereinbefore defined and $R^9$ represents an alkyl group of 1 to 4 carbon atoms, for example by means of di-isobutylaluminium hydride in a suitable solvent such as tetrahydrofuran and between $-30°$ C. and $+30°$ C.

Compounds of formula IX wherein X represents a vinylene group, and $R^1$, $R^2$, $R^4$ and $R^9$ are as hereinbefore defined, may be prepared from a compound of the general formula X shown at the end of the specification, wherein $R^1$, $R^2$ and $R^4$ are as hereinbefore defined, by a Wittig reaction, or variant thereof, for example by reaction with the anion of a trialkyl phosphonoacetate (generated in situ by treatment with a strong base, for example sodium hydride), in a suitable solvent such as tetrahydrofuran and at between $-20°$ C. and $50°$ C.

Compounds of formula IX wherein X represents an ethylene group, and $R^1$, $R^2$, $R^4$ are as hereinbefore defined, may be prepared by the catalytic reduction of corresponding compounds wherein X represents a vinylene group, under conditions similar to those described hereinbefore for the preparation of compounds of formula I wherein X represents an ethylene group by catalytic reduction.

Compounds of formula X, wherein $R^1$, $R^2$ and $R^4$ are as hereinbefore defined, may be prepared from a compound of the general formula XI shown at the end of the specification, wherein $R^1$, $R^2$ and $R^4$ are as hereinbefore defined and $R^{10}$ represents an alkyl group of 1 to 4 carbon atoms, by a series of reactions similar to those described hereinbefore for the preparation of compounds of formula VI from compounds of formula IX.

Compounds of formula XI, wherein $R^1$, $R^2$, $R^4$ and $R^{10}$ are as hereinbefore defined, may be prepared from a compound of the general formula XII shown at the end of the specification, wherein $R^1$ and $R^4$ are as hereinbefore defined, by reaction with a compound of the general formula:

$$R^2C\equiv CCOOR^{10} \qquad \text{XIII}$$

wherein $R^2$ $R^{10}$ and are as hereinbefore defined in a suitable solvent, for example acetonitrile or 1,3-dimethylimidazolin-2-one, at $10°-100°$ C.

Compounds of formula XII, wherein $R^1$ and $R^4$ are as hereinbefore defined, may be prepared from a compound of the general formula XIV shown at the end of the specification, wherein $R^1$ and $R^4$ are as hereinbefore defined, by reaction with a mixture of acetic acid and fluoroboric acid at $30°-80°$ C.

Compounds of formula XIV may be prepared by the application or adaptation of known methods, for example methods described by Popp & Soto, J. Chem. Soc., (1963), 1760.

Alternatively, compounds of formula XI, wherein $R^1$, $R^2$, $R^4$ and $R^{10}$ are as hereinbefore defined, may be prepared by the acid-catalysed hydrolysis and cyclisation of an acetal of the general formula XV shown at the end of the specification, wherein $R^1$, $R^2$, $R^4$ and $R^{10}$ are as hereinbefore defined and $R^{11}$ represents an alkyl group of 1 to 4 carbon atoms, in a strong acid, for example a mixture of concentrated sulphuric acid and glacial acetic acid, at $0°-50°$ C. Alternatively, this reaction may be carried out stepwise via the aldehyde corresponding to the acetal.

Compounds of formula XV, wherein $R^1$, $R^2$, $R^4$, $R^{10}$ and $R^{11}$ are as hereinbefore defined, may be prepared from a compound of the general formula XVI shown at the end of the specification, wherein $R^1$, $R^2$, $R^4$ and $R^{10}$ are as hereinbefore defined by reaction with a compound of the general formula:

$$Z^1CH_2CH(OR^{11})_2 \qquad \text{XVIIa}$$

wherein $R^{11}$ is as hereinbefore defined and $Z^1$ represents a halogen atom, in the presence of a suitable base, for example sodium hydroxide, and optionally in the presence of a phase transfer catalyst, for example tris[2-(2-methoxyethoxy)ethyl]amine, in a suitable solvent such as dimethylformamide, at $0°-50°$ C.

Alternatively, compounds of formula XV, wherein $R^1$, $R^2$, $R^4$, and $R^{11}$ are as hereinbefore defined, may be prepared from a compound of the general formula XVIII shown at the end of the specification, wherein $R^1$, $R^2$, $R^4$ and $R^{10}$ are as hereinbefore defined by reaction with a compound of the general formula:

$$NH_2CH_2CH(OR^{11})_2 \qquad \text{XVIIb}$$

wherein $R^{11}$ is as hereinbefore defined, optionally in the presence of acetic acid, and at $50°-170°$ C.

Compounds of formula XVIII, wherein $R^1$, $R^2$, $R^4$ and $R^{10}$ are as hereinbefore defined, may be prepared from a compound of the general formula:

$$R^2CH=C(COR^1)COOR^{10} \qquad \text{XIX}$$

wherein $R^1$, $R^2$, and $R^{10}$ are as hereinbefore defined, by reaction with a compound of the general formula XX shown at the end of the specification, wherein $R^4$ is as hereinbefore defined, in the presence of an organic base, e.g. triethylamine, and a suitable catalyst, e.g. 3,4-dimethyl-5-(2-hydroxyethyl)thiazolium iodide, in a suitable solvent, e.g. ethanol, and at $40°-80°$ C.

Compounds of formula XIX, wherein $R^1$, $R^2$, and $R^{10}$ are, as hereinbefore defined, may be prepared from a compound of the general formula:

$$R^1COCH_2COOR^{10} \qquad \text{XXI}$$

wherein $R^1$ and $R^{10}$ are as hereinbefore defined, by condensation with a compound of the general formula:

$$R^2CHO \qquad \text{XXII}$$

wherein $R^2$ is as hereinbefore defined, in the presence of a suitable catalyst, e.g. piperidinium acetate, and a suitable solvent, e.g. toluene, preferably at reflux, with azeotropic removal of water.

As an alternative, compounds of formula XV, wherein $R^1$, $R^2$, $R^4$, $R^{10}$ and $R^{11}$ are as hereinbefore defined, may be prepared from a compound of the general formula XXIII shown at the end of the specification, wherein $R^1$, $R^4$ and $R^{11}$ are as hereinbefore defined, by reaction with a compound of formula XIII (wherein $R^2$ and $R^{10}$ are as hereinbefore defined) in acetic anhydride and in the presence of a base, e.g. triethylamine, and at $0°-50°$ C.

Compounds of formula XXIII, wherein $R^1$, $R^4$ and $R^{11}$ are as hereinbefore defined, may be prepared by the hydrolysis of a compound of the general formula XXIV shown at the end of the specification, wherein $R^1$, $R^4$ and $R^{11}$ are as hereinbefore defined and represents an alkyl group of 1 to 4 carbon atoms, by known methods for the hydrolysis of esters, e.g. reaction with sodium hydroxide in aqueous methanol, followed by acidification, e.g. by means of hydrochloric acid.

Compounds of formula XXIV, wherein $R^1$, $R^4$, $R^{11}$ and $R^{12}$ are as hereinbefore defined, may be prepared from a compound of the general formula XXV shown at the end of the specification, wherein $R^4$, $R^{11}$ and $R^{12}$ are as hereinbefore defined, by reaction with a compound of the general formula:

$$R^1COZ^2 \qquad XXVI$$

wherein $R^2$ is as hereinbefore defined and $Z^2$ represents a halogen atom, in a suitable solvent such as dichloromethane and preferably in the presence of a base, e.g. triethylamine.

Compounds of formula XXV, wherein and $R^4$, $R^{11}$ and $R^{12}$ are as hereinbefore defined, may be prepared from a compound of the general formula XXVII shown at the end of the specification, wherein $R^4$ and $R^{12}$ are as hereinbefore defined and $Z^3$ represents a halogen atom, by reaction with a compound of formula XVIIb wherein $R^{11}$ is as hereinbefore defined, in a suitable solvent, e.g. acetonitrile, in the presence of a base, e.g. triethylamine, at 10°–50° C.

As a further alternative, compounds of formula XV, wherein $R^1$, $R^4$, $R^{10}$ and $R^{11}$ are as hereinbefore defined, and $R^2$ represents an optionally substituted aryl or heterocyclyl group, may be prepared from a compound of the general formula XXVIII shown at the end of the specification, wherein $R^4$ is as hereinbefore defined and $R^{13}$ represents an optionally substituted aryl or heterocyclyl group within the definition of $R^2$, by reaction with a compound of formula XVIIb (wherein $R^{11}$ is as hereinbefore defined) and a compound of the general formula:

$$R^1COCH_2COOR^{10} \qquad XXIX$$

wherein $R^1$ and $R^{10}$ are as hereinbefore defined, in the presence of a Lewis catalyst, e.g. zinc chloride, in a suitable solvent, e.g. ethanol, at 40°–80° C. Because of the possibility of production of mixtures of compounds, this process is more suitable for the preparation of compounds of formula XV wherein the symbols $R^4$ all represent hydrogen atoms, i.e. the compound of formula XXVIII is preferably benzoin.

Intermediate compounds of general formulae VII, XIII, XVI, XVIIa, XVIIb, XX, XXI, XXII, XXVI, XXVII, XXVIII AND XXIX, wherein the various symbols are as hereinbefore defined, are known or can be prepared by the application or adaptation of known methods.

The following Examples illustrate the preparation of compounds according to the present invention, and the Reference Examples illustrate the preparation of intermediates.

In the presentation of the nuclear magnetic resonance ("N.M.R.") spectra, "DMSO-d$_6$" means "deuterated dimethylsulphoxide", "s", "d", "t", "q" and "m" mean "singlet", "doublet", "triplet", "quartet" and "multiplet" respectively, "dd" means "doublet of doublets", "dt" means "doublet of triplets", "b" means "broad" and the positions of the signals are given in parts per million from the tetramethylsilane signal.

EXAMPLE 1

Compound A

A stirred solution of methyl (E)-5-hydroxy-7-(3-isopropyl-1-phenylpyrrolo[2,1-a]isoquinolin-2-yl)-3-oxohept-6-enoate (650 mg; prepared as described in Reference Example 1) in methanol (20 ml) was cooled to 0° C. and treated with sodium borohydride (30 mg). The mixture was stirred at 0° C. for 30 minutes and then it was poured into a mixture of ice and water (50 ml). The resulting mixture was extracted with diethyl ether (3×40 ml) and the ethereal extracts were combined, washed with brine, dried over magnesium sulphate and evaporated, and the residue was subjected to flash chromatography on silica gel using a mixture of dichloromethane and methanol (19:1 v/v) as eluent to give [2,1-a]isoquinolin-2-yl)hept-6-enoate (450 mg) in the form of a pale yellow solid, m.p. 146°–150° C. [N.M.R. (in CDCl$_3$ and D$_2$O): 1.50 (6H, d, J=7 Hz), 1.6–1.8 (2H, m), 2.4–2.5 (2H, m), 3.65 (1H, septet, J=7 Hz), 3.74 (3H, two s), 4.0–4.1 (1H, m), 4.25–4.4 (1H, m), 5.25 and 5.32 (1H, two dd, J=16 and 6 Hz), 6.61 and 6.65 (1H, two d, J=16 Hz), 6.70 (1H, d, J=8 Hz), 7.0–7.56 (9H, m), and 7.84 (1H, d, J=8 Hz)].

The N.M.R. spectrum indicated that the product was a 3:2 mixture of the erythro- and threo-diastereoisomers.

EXAMPLE 2

Compound B

A solution of a 3:2 mixture of the erythro- and threo.-diastereoisomers of methyl (E)-3,5-dihydroxy-7-(3-isopropyl-1-phenylpyrrolo[2,1-a]isoquinolin-2-yl)hept-6-enoate (300 mg; prepared as described in Example 1) and sodium hydroxide (26 mg) in a mixture of water (1 ml) and methanol (10 ml) was stirred under an atmosphere of argon at the ambient temperature for 2.5 hours. The solution was then evaporated in vacuo and the residue was washed with diethyl ether (5×20 ml). The residue was then dried by the following method. It was dissolved in methanol (20 ml) and the methanol was then evaporated in vacuo, and this was repeated twice more. Diethyl ether (20 ml) was then added and then evaporated in vacuo and this was repeated twice more. There was thereby obtained sodium (E)-3,5-dihydroxy-7-(3-isopropyl-1-phenylpyrrolo[2,1-a]isoquinolin-2-yl)hept-6-enoate (260 mg) in the form of a buff solid, m.p. 213°–217° C. (with decomposition). [N.M.R. (in DMSO$_6$ and D$_2$O): 1.1–1.3 (2H, m), 1.46 (6H, d, J=7 Hz), 1.75–2.1 (2H, m), 3.53–3.79 (2H, m), 4.02–4.15 (1H, m), 5.24 and 5.27 (1H, two dd, J=16 and 6 Hz), 6.45 (1H, dd, J=16 and 1 Hz), 6.82 (1H, d, J=8 Hz), 7.0–7.61 (9H, m), and 8.1 (1H, d, J=8 Hz). The N.M.R. spectrum indicated that the product was a 2:1 mixture of the erythro- and threo-diastereoisomers].

EXAMPLE 3

Compound C

By proceeding in a manner similar to that described hereinbefore in Example 1, but replacing the methyl (E)-5-hydroxy-7-(3-isopropyl-1-phenylpyrrolo-[2,1a]isoquinolin-2-yl)-3-oxohept-6-enoate used as starting material by the appropriate quantity of ethyl (E)-5-hydroxy-7-(3-isopropyl-1-phenylpyrrolo[2,1-a]-isoquinolin-2-yl)-3-oxohept-6-enoate, prepared as described in Reference Example 2, there was prepared a mixture of the erythro- and threo-diastereoisomers of ethyl (E)-3,5-dihydroxy-7-(3-isopropyl-1-phenylpyrrolo[2,1-a]isoquinolin2-yl)hept-6-enoate, in the form of a yellow gum.

EXAMPLE 4

Compound D

A mixture of ethyl (E)-3,5-dihydroxy-7-(3-isopropyl-1-phenylpyrrolo[2,1-a]isoquinolin-2-yl)hept-6-enoate (157 mg; prepared as described in Example 3), activated manganese dioxide (1.74 g) and diethyl ether (25 ml) was stirred at the ambient temperature under an argon atmosphere for 2 hours. The suspension was then filtered and the solid was extracted with diethyl ether (3×15 ml). The filtrate was combined with the extracts and evaporated in vacuo, to give ethyl (E)-3-hydroxy-7-(3-isopropyl-1-phenylpyrrolo[2,1-a]-isoquinolin-2-yl)-5-oxohept-6-enoate (80 mg), in the form of an orange gum. [N.M.R. (in CDCl$_3$): 1.26 (3H, t, J=7 Hz), 1.55 (6H, d, J=7 Hz), 2.48 (2H, d, J=7 Hz), 2.55 (2H, d, J=7 Hz), 3.76 (1H, septet, J=7 Hz), 4.19 (2H, q, J=7 Hz), 4.41 (1H, quintet, J=7 Hz), 5.71 (1H, d, J=16 Hz), 6.73 (1H, d, J=8 Hz), 7.01–7.59 (9H, m), 7.03 (1H, d, J=8 Hz), 7.04 (1H, d, J=16 Hz); Mass spectrum (electron impact) m/e =469].

EXAMPLE 5

Compound E

A mixture of sodium hydroxide (120 mg), water (2 ml), methanol (10 ml) and ethyl (E)-3-hydroxy-7-(3-isopropyl-1-phenylpyrrolo[2,1-a]isoquinolin-2-yl)-5-oxohept-6-enoate (230 mg; prepared as described in Example 4) was stirred under an argon atmosphere at the ambient temperature for 5 hours. Water (10 ml) was added and the solution was acidified to pH 5 by treatment with glacial acetic acid. The milky solution was extracted with diethyl ether (4×50 ml) and the combined extracts were dried over magnesium sulphate and evaporated, to give (E-3-hydroxy-7-(3-isopropyl-1-phenylpyrrolo[2,1-a]isoquinolin-2-yl)-5-oxohept-6-enoic acid, (80 mg) in the form of a buff foam, m.p. 95°–100° C. [Elemental analysis: C 76.7; H, 6.57; N, 3.02%; Calculated: C, 76.2; H, 6.16; N, 3.2%. N.M.R. (in CDCl$_3$ and D$_2$O): 1.56 (6H, d, J=7 Hz), 2.54 (2H, d, J=7 Hz), 2.55 (2H, d, J=7 Hz), 3.76 (1H, septet, J=7 Hz), 4.42 (1H, quintet, J=7 Hz), 5.68 (1H, d, J=16 Hz), 6.75 (1H, d, J=8 Hz), 7.03–7.57 (9H, m), 7.84 (1H, d, J=8 Hz), 7.86 (1H, d, J=16 Hz)].

EXAMPLE 6

Compound F

Sodium borohydride (38 mg) was added to a stirred solution of ethyl 5-hydroxy-7-(3-isopropyl-1-phenylpyrrolo[2,1-a]isoquinolin-2-yl)-3-oxoheptanoate (760 mg; prepared as described in Reference Example 3) in methanol (20 ml) at 0° C. under an argon atmosphere. The mixture was stirred at 30 minutes and then a solution of sodium hydroxide (320 mg) in water (8 ml) was added and the mixture was stirred for 1 hour. The mixture was then diluted with water (20 ml) and acidified with glacial acetic acid. The resulting milky solution was extracted with diethyl ether (3×50 ml) and the combined extracts were dried over magnesium sulphate and evaporated, to give 3,5-dihydroxy-7-(3-isopropyl-1-phenylpyrrolo[2,1-a]-isoquinolin-2-yl)heptanoic acid (730 mg), in the form of a yellow gum.

EXAMPLE 7

Compound G

A solution of 3,5-dihydroxy-7-(3-isopropyl-1-phenylpyrrolo[2,1-a]isoqu-inolin-2-yl)heptanoic acid (712 mg; prepared as described in Example 6) in toluene (100 ml), containing glacial acetic acid (5 drops), was heated with stirring at 100° C. for 4 hours. The solution was then evaporated in vacuo to give an orange gum, which was subjected to flash chromatography on silica gel, using as eluant a mixture of dichloromethane and methanol (19:1 v/v), to give a 1:2 mixture of the cis- and translactone ring isomers of 4-hydroxy-6-[2-(3-isopropyl 1-phenylpyrrolo[2,1-a]isoquinolin-2-yl)ethyl]-3,4,5,6-tetrahydro-2H-pyran-2-one (310 mg), in the form of a yellow foam, m.p. 99°–102° C. [Elemental analysis: C, 78.8; H, 7.0; N, 3.0%; Calculated: C, 78.7; H, 6 84; N, 3.28%; N.M.R. (in CDCl$_3$ and D$_2$O): 1.50 (6H, d, J=7 Hz), 1.5–2.2 (4H, m), 2.34–2.88 (4H, m), 3.57 (1H, d, septet, J=2 Hz, 7 Hz), 3.9–4.16, 4.2–4.32, 4.44–4.6 (2H, 3×m), 6.69 (1H, d, J=8 Hz), 7.0–7.55 (9H, m), 7.85 (1H, d, J=8 Hz); Mass spectrum (electron impact) m/e=427].

EXAMPLE 8

Compound H

By proceeding in a manner similar to that described hereinbefore in Example 1, but replacing the methyl (E)-5hydroxy-7-(3-isopropyl-1-phenylpyrrolo-[2,1-a]isoquinolin-2-yl)-3-oxohept-6-enoate used as starting material by the appropriate quantity of ethyl (E)-5-hydroxy-7-(3-methyl-1-phenylpyrrolo[2,1-a]-isoquinolin-2-yl)-3-oxohept-6-enoate, prepared as described in Reference Example 4, there was prepared ethyl (E)-3,5-dihydroxy-7-(3-methyl-1-phenylpyrrolo-2,1-a]isoquinolin-2-yl)hept-6-enoate, in the form of a gum. [N.M.R. (in CDCl$_3$): 1.20–1.34 (3H, t, J=7 Hz), 1.40–1.80 (2H, m), 2.46 (2H, m), 2.56 (3H, s), 4.10–430 (3H, m), 4.30–4.46 (1H, m), 5.46 and 5.50 (1H, dd, J=7 and 16 Hz), 6.51 and 6.54 (1H, d, J=16 Hz), 6.76 (1H, d, J=8 Hz), 7.08 (1H, dt, J=2 and 8 Hz), 7.14–7.28 (1H, m), 7.30–7.60 (7H, m), 7.62 (1H, d, J=8 Hz)].

EXAMPLE 9

Compound I

By proceeding in a manner similar to that described hereinbefore in Example 2, but replacing the methyl (E)-3,5-dihydroxy-7-(3-isopropyl-1-phenylpyrrolo-[2,1-a]isoquinolin-2-yl)hept-6-enoate used as starting material by the appropriate quantity of ethyl (E)-3,5-dihydroxy-7-(3-methyl-1-phenylpyrrolo[2,1-a]-isoquinolin-2-yl)hept-6-enoate, prepared as described in Example 8, there was prepared sodium (E)-3,5-dihydroxy-7-(3-methyl-1-phenylpyrrolo[2,1-a]isoquinolin-2-yl)hept6-enoate, in the form of a brown powder. [N.M.R. (in DMSO-d$_6$: 1.10–1.60 (2H, m). 1.70–2.10 (2H, m), 2.55 (3H, s), 3.10–3.85 (1H, m), 4.00–4.20 (1H, m), 4.60–4.95 (1H, b), 5.43 and 5.48 (1H, dd, J=6 and 16 Hz), 6.35 (1H, d, J=16 Hz), 6.91 (1H, d, J=7 Hz), 7.00–7.70 (9H, m), 7.97 (1H, d, J=7 Hz)].

EXAMPLE 10

Compound J

By proceeding in a manner similar to that described hereinbefore in Example 1, but replacing the methyl (E)-5-hydroxy-7-(3-isopropyl-1-phenylpyrrolo-[[2,1-a]isoquinolin-2-yl)-3-oxohept-6-enoate used as starting material by the appropriate quantity of ethyl (E)-5-hydroxy-7-{3-ethyl-1-(4-fluorophenyl)pyrrolo-[2,1-a]-isoquinolin-2-yl)-3-oxohept-6-enoate, prepared as described in Reference Example 5, there was prepared ethyl (E)-3,5-dihydroxy-7{3-ethyl-1-(4-fluorophenyl)-pyrrolo[ 2,1-a[isoquinolin-2-yl)hept-6 TM enoate. [N.M.R. (in CDCl$_3$): 1.20–1.39 (6H, m), 1.50–1.80 (2H, m), 2.48 (2H, m), 4.19 (2H, q, J=7 Hz), 4.30–4.50 (1H, m), 5.46 and 5.50 (1H, dd, J=6 and 16 Hz), 6.48 and 6.50 (1H, dd, J=2 and 16 Hz), 6.75 (1H, d, J=7 Hz), 7.00–7.44 (7H m), 7.48 (1H, d, J=7 Hz), 7.67 (1H, d, J=7 Hz)].

EXAMPLE 11

Compound K

By proceeding in a manner similar to that described hereinbefore in Example 2, but replacing the methyl (E)-3,5-dihydroxy-7-(3-isopropyl-1-phenylpyrrolo-[2,1a]isoquinolin-2-yl)hept-6-enoate used as starting material by the appropriate quantity of ethyl (E)-3,5-dihydroxy-7-{3ethyl-1-(4-fluorophenyl)pyrrolo-[2,1-a]isoquinolin-2-yl}hept-6-enoate, prepared as described in Example 10, there was prepared sodium (E)-3,5-dihydroxy-7-{3-ethyl-1-(4-fluorophenyl)pyrrolo-[2,1-a]isoquinolin-2-yl}hept-6-enoate, in the form of a brown powder, m.p. 217°–221° C. [N.M.R. (in DMSO-d$_6$): 1.10–1.60 (4H, m). 1.70–2.20 (2H, m), 3.05 (2H, q, J=7 Hz), 3.56–3.84 (1H, m), 4.01–4.09 (1H, m), 4.60–5.00 (1H, bm), 5.42 and 5.45 (1H, dd, J=6 and 16 Hz), 6.31 (1H, d, J=16 Hz), 6.90 (1H, d, J=7 Hz), 7.04–7.56 (7H, m), 7.62 (1H, d, J=6 Hz), 8.03 (1H, d, J=7 Hz)].

EXAMPLE 12

Compound L

By proceeding in a manner similar to that described hereinbefore in Example 1, but replacing the methyl (E)-5-hydroxy-7-(3-isopropyl-1-phenylpyrrolo-[2,1-a]isoquinolin-2-yl)-3-oxohept-6-enoate used as starting material by the appropriate quantity of ethyl (E)-5-hydroxy-7-{1-isopropyl-3-(4-fluorophenyl)pyrrolo-[2,1-a-isoquinolin-2-yl}-3-oxohept-6-enoate, prepared as described in Reference Example 6, there was prepared ethyl (E)-3,5-dihydroxy-7-{1-isopropyl-3-(4-fluorophenyl)pyrrolo[2,1-a]isoquinolin-2-yl}hept-6-enoate in the form of a colourless viscous oil. [N.M.R. (in CDCl$_3$ and D$_2$O): 1.27 (3H, t, J=7 Hz), 1.4–1.7 (8H, m), 2.39–2 47 (2H, m), 4.0 (1H, septet, J=7 Hz), 4.05–4.15 (3H, m), 4.34–4.46 (1H, m), 5.3 and 5.37 (1H, two dd, J=6 and 16 Hz), 6.55 (1H, d, J=8 Hz), 6.82 and 6.84 (1H, two dd, J=1 and 16 Hz), 7.1–7.52 (8H, m), 8.25 (1H, d, J=8 Hz). The N.M.R. spectrum indicated that the product was a 3:2 mixture of the erythro- and threo-diastereoisomers].

EXAMPLE 13

Compound M

By proceeding in a manner similar to that described hereinbefore in Example 2, but replacing the methyl (E)-3,5-dihydroxy-7-(3-isopropyl-1-phenylpyrrolo-[2,1-a]isoquinolin-2-yl)hept-6-enoate used as starting material by the appropriate quantity of ethyl (E)-3,5-dihydroxy-7-{1-isopropyl-3-(4-fluorophenyl)pyrrolo[2,1-a]isoquinolin-2-yl}hept-6-enoate, prepared as described in Example 14, there was prepared sodium (E)-3,5dihydroxy-7-{1-isopropyl-3-(4-fluorophenyl)pyrrolo-[2,1-a]isoquinolin-2-yl}hept-6-enoate, in the form of a pale yellow solid, m.p. 225° C. (with decomposition). [Elemental analysis: C,67.4;H,5.7;N,2.7;HO,3.6%; calculated: C,67.1;H,5.8;N,2.8;H$_2$O,3.6%; N.M.R. (in DMSO$_6$ and D$_2$O): 1.05–1.4 (2H, m), 1.47 (6H, d, J=7 Hz), 1.7–2.05 (2H, m), 3.5.3.8 (1H, m), 3.97 (1H, septet, J=7 Hz), 4.0–4.19 (1H, m), 5.28 and 5.31 (1H, two dd, J=6 and 16 Hz), 6.63 (1H, d, J=16 Hz), 6.72 (1H, d, J=8 Hz), 7.27–7.63 (8H, m), 8.21 (1H, d, J=8 Hz). The N.M.R. spectrum indicated that the product was a 3:2 mixture of the erythro- and threo-diastereoisomers-].

EXAMPLE 14

Compounds N, NA and NB

By proceeding in a manner similar to that described hereinbefore in Example 1, but replacing the methyl (E)-5-hydroxy-7-(3-isopropyl-1-phenylpyrrolo-[2,1-a]isoquinolin-2-yl)-3-oxohept-6-enoate used as starting material by the appropriate quantity of ethyl (E)-5-hydroxy-7-{3-isopropyl1-(4-fluorophenyl)pyrrolo-[2,1-a]-isoquinolin-2-yl}-3-oxohept-6-enoate, prepared as described in Reference Example 7, there was prepared ethyl (E)-3,5-dihydroxy-7-{3-isopropyl-1-4-fluorophenyl)pyrrolo[2,1a]isoquinolin-2-yl}hept-6-enoate in the form of a yellow gum.

A portion of this material (1.0g) was subjected to h.p.l.c. on a silica gel column, using a mixture of hexane, ethyl acetate and methanol (90:9.5:0.5 v/v) as eluent, to give ethyl erythro-(E)-3,5-dihydroxy-7-{3-isopropyl-1-(4-fluorophenyl)pyrrolo[2,1-a]-isoquinolin-2-yl}hept-6-enoate (0.34g) in the form of a pale yellow gum [N.M.R. (in CDCl and D$_2$O): 1.28 (3H, t, J=7 Hz), 1.32–1.68 (8H, m), 2.42–2.48 (2H, m), 3.64 (1H, septet, J=7 Hz), 4.08–4.25 (3H, m), 4.30–4.42 (1H, bm), 5.25 (1H, dd, J=6 and 16 Hz), 6.59 (1H, dd, J=1 and 16 Hz), 6.69 (1H, d, J=8 Hz), 70.1–7.52 (8H, m), 7.82 (1H, d, J=8 Hz)]; and ethyl threo-(E)-3,5-dihydroxy-7-{3-isopropyl-1-(4-fluorophenyl)pyrrolo[2,1-a]-isoquinolin-2-yl}hept-6-enoate (0.28 g) in the form of a pale yellow gum [N.M.R. (in CDCl$_3$ and D$_2$O): 1.28 (3H, t, J=7 Hz), 1.36–1.75 (8H, m), 2.39–2.46 (2H, m), 3.63 (1H, septet, J=7 Hz), 4.06–4.25 (3H, m), 4.32–4.44 (1H, bm), 5.32 (1H, dd, J=6 and 16 Hz), 6639 (1H, dd, J=1 and 16 Hz), 6.69 (1H, d, J=8 Hz), 70.1–7.51 (8H, m), 7.82 (1H, d, J=8 Hz)].

EXAMPLE 15

Compounds O, OA and OB

By proceeding in a manner similar to that described hereinbefore in Example 2, but replacing the methyl (E)-3,5-dihydroxy-7-(3-isopropyl-1-phenylpyrrolo-[2,1-a]isoquinolin-2-yl)hept-6-enoate used as starting material by the appropriate quantity of ethyl (E)-3,5-dihydroxy-7-{3-isopropyl-1-(4-fluorophenyl)pyrrolo[2,1-a]isoquinolin-2-yl}hept-6-enoate, prepared as described in Example 14, there was prepared sodium (E)-3,5-dihydroxy-7-{3-isopropyl-1-(4-fluorophenyl)pyrrolo[2,1-a]isoquinolin-2-yl)hept-6-enoate,in the form of a buff solid, m.p. 207°–210° C. (with decomposition). [Elemental analysis: C,66.3;H,6.3;N,2.5;H$_2$O, 4.5%; calculated: C,65.9;H,5.93;N,2.7;H$_2$O, 5.3%; N.M.R. (in DMSO-d$_6$ and D$_2$O): 1.1–1.3 (2H, m), 1.46 (6H, d, J=6 Hz), 1.72–2.08 (2H, m), 3.5–3.8 (2H, m), 4.0–4.15 (1H, m), 5.19 and 5.25 (1H, two dd, J=6 and 16 Hz), 6.44 (1H, dd, J=1 and 16 Hz), 6.85 (1H, d, J=8 Hz), 7.05–7.63 (8H, m), 8.13 (1H, d, J=8 Hz). The N.M.R. spectrum indicated that the product was a 3:2 mixture of the erythro- and threo-diastereoisomers].

By proceeding in a similar manner, but using the separated erythro- and threo-diastereoisomers prepared as described hereinbefore in Example 14, there were prepared sodium erythro-(E)-3,5-dihydroxy-7-{3-isopropyl-1-(4-fluorophenyl)pyrrolo-[2,1-a]isoquinolin-2-yl}hept-6-fluoropenoate, in the form of a buff solid, m.p. 215°–220° C. (with decomposition) [N.M.R. (in DMSO-$d_6$ and $D_2O$): 1.04–1.3 (2H, m), 1.45 (6H, d, J=7 Hz), 1.74–2.10 (2H, m), 3.54–3.78 (2H, m), 4.01–4.16 (1H, m), 5.2 (1H, dd, J=6 and 16 Hz), 6.44 (1H, dd, J=16 Hz), 6.85 (1H, d, J=8 Hz), 7.04–7.64 (8H, m), 8.12 (1H, d, J=8 Hz)]; and sodium threo-(E)-3,5-dihydroxy-7-{3-isopropyl-1-(4-fluorophenyl)pyrrolo-[2,1-a]isoquinolin-2-yl}hept-6-enoate, in the form of a buff solid, m.p. 218°–223° C. (with decomposition). [N.M.R. (in DMSO-$d_6$ and $D_2O$): 1.04–1.3 (2H, m), 1.45 (6H, d, J=7 Hz), 1.72–2.06 (2H, m), 3.54–3.82 (2H, m), 4.02–4.17 (1H, m), 5.25 (1H, dd, J=6 and 6 Hz), 6.45 (1H, dd, J=16 Hz), 6.84 (1H, d, J=8 Hz), 7.01–7.64 (8H, m), 8.12 (1H, d, J=8 Hz)].

EXAMPLE 16

Compound P

By proceeding in a manner similar to that described hereinbefore in Example 4 but replacing the ethyl (E)-3,5-dihydroxy-7-(3-isopropyl-1-phenylpyrrolo-[2,1-a]isoquinolin-2-yl)hept-6-enoate used as starting material by the appropriate quantity of ethyl (E)-3,5-dihydroxy-7-{3-isopropyl-1-(4-fluorophenyl)pyrrolo[2,1-a]isoquinolin-2-yl}hept-6-enoate, prepared as described in Example 14, there was prepared ethyl (E)-3-hydroxy-7-{3-isopropyl-1-(4-fluorophenyl)pyrrolo-[2,1-a]isoquinolin-2-yl}-5-oxohept-6-enoate in the form of an amber oil. [N.M.R. (in CDCl$_3$): 1.28 (3H, t, J=7 Hz), 1.54 (6H, d, J=8 Hz), 2.55 (4H, m), 3.62 (1H, d, J=3 Hz), 3.77 (1H, septet, J=8 Hz), 4.18 (2H, q, J=7 Hz), 4.45 (1H, m), 5.73 (1H, d, J=16 Hz), 6.76 (1H, d, J=8 Hz), 7.16–7.54 (8H, m), 7.77–7.90 (2H, m)].

EXAMPLE 17

Compound Q

By proceeding in a manner similar to that described hereinbefore in Example 2, but replacing the methyl (E)-3,5-dihydroxy-7-(3-isopropyl-1-phenylpyrrolo-[2,1-a]isoquinolin-2-yl)hept-6-enoate used as starting material by the appropriate quantity of ethyl (E)-3-hydroxy-7-{3isopropyl-1-(4-fluorophenyl)pyrrolo-[2,1-a]isoquinolin-2-yl}-5-oxohept-6-enoate, prepared as described in Example 16, there was prepared sodium (E)-3-hydroxy-7-{3-isopropyl-1-(4-fluorophenyl)pyrrolo-[2,1-a]isoquinolin-2-yl}-5-oxohept-6-enoate, in the form of a golden brown solid, m.p. 140° C. (with decomposition). [Elemental analysis: C,67.4;H,5.37;N,2.73;F,3.59; $H_2O$,2.9%; calculated: C,67.33;H,5.45;N,2.80; F,3.81; $H_2O$,3.6%].

REFERENCE EXAMPLE 1

(a) An aqueous solution of fluoroboric acid (48% w/v; 33 ml) was added to a stirred solution of 1-cyano-2-isobutyryl-1,2-dihydroisoquinoline (6.78 g; prepared according to the method described by F. D. Popp and A. Soto, J. Chem. Soc., 1963, 1760) in acetic acid (25 ml) at 60° C. The solution was stirred for 15 minutes and then cooled to 5° C. The solid was collected, washed thoroughly with diethyl ether and dried, to give 1-amino-3-isopropyloxazolo[4,3-a]isoquinolinium tetrafluoroborate (8.55 g) in the form of a pale yellow solid, m.p. 181°–183° C. [Elemental analysis: C, 53.0; H, 4.78; N, 8.9%; Calculated: C, 53.5; H, 4.81; N, 8 9%; N.M.R. in CD$_3$CN): 1.44 (6H, d, J=7 Hz), 3.68 (1H, septet, J=7 Hz), 5.90 (2H, broad s), 7.27 (1H, d, J=8 Hz), 7.48–7.72 (4H, m), 7.92 (1H, d, J=8 Hz); Mass spectrum (fast atom bombardment) m/e=227].

(b) Ethyl phenylpropiolate (10.1 g, 0.058 mol) was added with stirring to a solution of 1-amino-3-isopropyloxazolo[4,3-a]isoquinolinium tetrafluoroborate (9.1 g) in acetonitrile (90 ml) at 50° C. The solution was then heated at reflux for 30 minutes and it was then evaporated in vacuo to give a viscous orange-brown oil, which was extracted with hot petroleum ether (b.p. 60°–80° C.)(4×100 ml). The petroleum extract was evaporated in vacuo and the residue was subjected to flash chromatography on silica gel using as eluent a mixture of petroleum ether (b.p. 40°–60° C.) and diethyl ether (19:1 v/v), giving an oil, which crystallised on standing, to give ethyl 3-isopropyl-1-phenylpyrrolo-[2,1-a]isoquinoline-2-carboxylate (1.7 g), in the form of a colourless solid, m.p. 82°–84° C. [N.M.R. (in CDCl$_3$): 0.88 (3H, t, J=7 Hz), 1.52 (6H, d, J=7 Hz), 4.01 (2H, q, J=7 Hz), 4.14 (1H, septet, J=7 Hz), 6.75 (1H, d, J=8 Hz), 7.00–7.50 (9H, m), and 7.85 (1H, d, J=8 Hz)].

(c) A solution of ethyl 3-isopropyl-1-phenylpyrrolo-[2,1-a]isoquinoline-2-carboxylate (6.25 g) in anhydrous diethyl ether (100 ml) was added to a stirred suspension of lithium aluminum hydride (2.7 g) in diethyl ether (160 ml) at −2° C. under an atmosphere of argon. The mixture was stirred at between −5° and 0° C. for 5 hours and then the reaction mixture was quenched by the dropwise addition of ethyl acetate (50 ml), followed by dilute hydrochloric acid (100 ml; 1N), maintaining the temperature below 10° C. The organic phase was then separated. The aqueous phase was extracted with dichloromethane (2×150 ml) and the organic solutions were combined, washed with brine (300 ml), dried over magnesium sulphate and evaporated, to give 2-hydroxymethyl-3-isopropyl-1-phenylpyrrolo[2,1-a]-isoquinoline (5.1 g) in the form of a sticky yellow solid. [N.M.R. (in DMSO-$d_6$): 1.48 (6H, d, J=7 Hz), 3.65 (1H, septet, J=7 Hz), 4.3 (2H, d, J=4 Hz), 4.5 (1H, broad t, J=4 Hz), 6.85 (1H, d, J=8 Hz), 7.0–7.7 (9H, m), and 8.1 (1H, d, J=8 Hz)].

(d) A mixture of 2-hydroxymethyl--3-isopropyl-1phenylpyrrolo-[2,1-a]isoquinoline (2.05 g), activated manganese dioxide (22.56 g) and diethyl ether (120 ml) was stirred at the ambient temperature under an atmosphere of argon for 16 hours. The suspension was then filtered, the filtrate was evaporated and the resulting residue was subjected to flash chromatography on silica gel, using as eluent a mixture of petroleum ether (b.p. 40°–60° C.) and diethyl ether (3:1 v/v), to give 3-isopropyl-1-phenylpyrrolo[2,1-a]isoquinoline-2-carboxaldehyde (1.3 g) in the form of a yellow solid, m.p. 134°–136° C. [N.M.R. (in CDCl$_3$): 1.54 (6H, d, J=7 Hz), 4.30 (1H, septet, J=7 Hz), 6.82 (1H, d, J=8 Hz), 7.06–7.54 (9H, m), 7.89 (1H, d, J=8 Hz) and 9.76 (1H, s); Mass spectrum (electron impact) m/e=313].

(e) A dispersion of sodium hydride in oil (80%; 12 mmol) was washed with hexane and then dried in a stream of argon. The sodium hydride was then suspended in dry tetrahydrofuran (20 ml) and the suspension was cooled to between −15° C. and −9° C. Triethyl phosphonoacetate [2.7 g] was then added dropwise to the suspension under argon and the mixture was stirred for 45 minutes. The mixture was then treated, dropwise, with a solution of 3-isopropyl-1-phenylpyrrolo[2,1-a]isoquinoline-2-carboxaldehyde (2.5 g) in dry tetrahydrofuran (40 ml), maintaining the temperature at between −15° C. and −9° C. The mixture was stirred at between −15° C. and −9° C. under argon for 45 minutes, and then it was allowed to warm to 20° C. The reaction mixture was then quenched by the addition of saturated aqueous ammonium chloride solution (50 ml). The mixture was treated with diethyl ether (50 ml). The organic layer was then separated, washed with brine (50 ml), dried over magnesium sulphate, and evaporated, to give a yellow oil which was subjected to flash chromatography on silica gel using as eluent a mixture of petroleum ether (b.p. 40°–60° C.) and diethyl ether (3:1 v/v), to give ethyl (E)-3-(3-isopropyl-1-phenylpyrrolo[2,1-a]isoquinolin-2-yl)propenoate (2.66 g), in the form of a colourless solid, m.p. 145°–146° C. [Elemental analysis: C, 81.5; H, 6.61; N, 3.58%; calculated: C, 81.4; H, 6.57; N, 3.7%; N.M.R. (in $CDCl_3$): 1.24 (3H, t, J=7 Hz), 1.56 (6H, d, J=7 Hz), 3.78 (1H, septet, J=7 Hz), 4.16 (2H, q, J=7 Hz), 5.42 (1H, d, J=16 Hz), 6.73 (1H, d, J=8 Hz), 7.02–7.58 (9H, m), 7.86 (1H, d, J=8 Hz), 7.89 (1H, d, J=16 Hz); Mass spectrum (electron impact) m/e=383].

(f) A solution of diisobutyl aluminium hydride in toluene (1.5M; 16.8 ml) was added dropwise to a stirred solution of ethyl (E)-3-(3-isopropyl-1-phenylpyrrolo[2,1-a]isoquinolin-2-yl)propenoate (2.4 g) in dry tetrahydrofuran (50 ml) at 0° C. under an atmosphere of argon. The mixture was stirred at 0° C. for 30 minutes and then the reaction mixture was quenched by the dropwise addition of saturated aqueous sodium sulphate solution (50 ml) at 0° C. The resulting gel was then allowed to warm to 20° C. and it was then treated with sufficient aqueous hydrochloric acid (2N) to dissolve the gel. The organic phase was separated and the aqueous phase was extracted with diethyl ether (50 ml). The organic solutions were combined, washed with brine, dried over magnesium sulphate and evaporated, to give (E)-3-(3-isopropyl1-phenylpyrrolo[2,1-a]isoquinolin-2-yl)propen-1-ol in the form of an orange oil (2.14 g).

(g) A mixture of activated manganese dioxide (17.4 g), (E)-3-(3-isopropyl1-phenylpyrrolo[2,1-a]isoquinolin-2-yl)propen-1-ol (2.14 g) and anhydrous diethyl ether (50 ml) was stirred at 20° C. under an atmosphere of argon for 17 hours. The suspension was then filtered and the filtrate was evaporated to give an orange-red oil. The oil was triturated with a mixture of petroleum ether (b.p. 40°–60° C.) and diethyl ether (1:1 v/v). The resulting crystalline solid was collected, washed with a mixture of petroleum ether (b.p. 40°–60° C.) and diethyl ether (1:1 v/v) and dried to give (E)-3-(3-isopropyl-1-phenylpyrrolo[2,1-a]isoquinolin-2-yl)propenal (1.8 g), in the form of a yellow solid, m.p. indistinct, approximately 170° C. [N.M.R. (in $CDCl_3$): 1.6 (6H, d, J=7 Hz), 3.76 (1H, septet, J=7 Hz), 5.72 (1H, dd, J=8 Hz and 16 Hz), 6.75 (1H, d, J=8 Hz), 7.0–7.6 (9H, m), 7.15 (1H, d, J=16 Hz), 7.82 (1H, d, J=8 Hz), 9.43 (1H, d, J=8 Hz); Mass spectrum, m/e=340 (M+H+)]

(h) A dispension of sodium hydride in oil (80%, 12 mmol) was washed with hexane and then dried in a stream of argon. The sodium hydride was then suspended in dry tetrahydrofuran (40 ml) and stirred at −10° C. under an atmosphere of argon. Methyl acetoacetate (1.23 g) was then added dropwise at −10° C. and the mixture was stirred for a further period of 30 minutes. A solution of butyl lithium in hexane (6.2 ml; 1.6M) was then added dropwise at TM 10° C. and the mixture was stirred for 15 minutes. A solution of (E)-3-(3-isopropyl-1-phenylpyrrolo[2,1a]isoquinolin-2-yl)propenal (1.8 g) in tetrahydrofuran (8 ml) was then added dropwise at −10° C. and the mixture was stirred for 1 hour. The reaction mixture was than quenched at −10° C. by the addition of saturated aqueous ammonium chloride solution, and the mixture was allowed to warm to 20° C. The organic layer was separated and evaporated in vacuo and the residue was partitioned between diethyl ether (100 ml) and water (100 ml). The ethereal solution was separated and the aqueous phase was extracted with diethyl ether (50 ml). The ethereal solutions were combined, washed with brine, dried over magnesium sulphate, and evaporated in vacuo to give an orange oil, which was subjected to flash chromatography on silica gel, using a mixture of petroleum ether (b.p. 40°–60° C.) and diethyl ether as eluent, to give methyl (E)-5-hydroxy-7-(3-isopropyl-1-phenylpyrrolo[2,1-a]isoquinolin-2-yl)-3-oxohept-6-enoate (1.4 g) in the form of a yellow gum. [N.M.R. (in $DCDl_3$): 1.50 (6H, d, J=7 Hz), 2.48 (1H, broad s), 2.54–2.6 (2H, m), 3.45 (2H, s), 3.64 (1H, septet, J=7 Hz), 3.74 (3H, s), 4.54 (1H, m), 5.21 (1H, dd, J=16 Hz and 6 Hz), 6.64 (1H, d, J=16 Hz), 6.70 (1H, d, J=8 Hz), 7.0–7.54 (9H, m), 7.83 (1H, d, J=8 Hz)].

REFERENCE EXAMPLE 2

By proceeding in a manner similar to that described hereinbefore in Reference Example 1(h), but replacing the methyl acetoacetate used as a starting material by the appropriate quantity of ethyl acetoacetate, there was prepared ethyl (E)-5-hydroxy-7-(3-isopropyl-1-phenylpyrrolo[2,1-a]isoquinolin-2-yl)-3-oxohept-6-enoate (7.34 g) in the form of a pale yellow oil. [N.M.R. (in $CDCl_3$ and $D_2O$): 1.26 (3H, t, J=7 Hz), 1.50 (6H, d, J=7 Hz), 2.53–2.59 (2H, m), 3.43 (2H, s), 3.64 (1H, septet, J=7 Hz), 4.20 (2H, q, J=7 Hz), 4.54 (1H, m), 5.22 (1H, dd, J=16 Hz and 7 Hz), 6.64 (1H, dd, J=16 Hz and 1 Hz), 6.70 (1H, d, J=8 Hz), 7.0–7.54 (9H, m), 7.83 (1H, d, J=8 Hz)].

REFERENCE EXAMPLE 3

A solution of ethyl (E)-5-hydroxy-7-(3-isopropyl-1-phenylpyrrolo[2,1-a]isoquinolin-2-yl)-3-oxohept-6-enoate (0.94 g; prepared as described in Reference Example 2) in ethanol (42 ml) was reduced catalytically under a hydrogen atmosphere using 5% w/w palladium on charcoal (0.254 g) and 5% w/w palladium on calcium carbonate (0.226 g) as catalysts. The mixture was filtered to remove the catalysts and the filtrate was evaporated, to give ethyl 5-hydroxy-7-(3-isopropyl1-phenylpyrrolo[2,1-a]isoquinolin-2-yl)-3-oxoheptanoate (0.98 g) in the form of a pale green gum.

REFERENCE EXAMPLE 4

(a) A mixture of benzoin (10.6 g), ethyl acetoacetate (8.1 g), aminoacetaldehyde dimethyl acetal (6.3 g), zinc chloride (13.8 g) and ethanol (100 ml) was stirred at reflux for 40 hours. The mixture was then poured into water (800 ml) and stirred until a fine solid had formed. The product was filtered off, washed with water and dried in vacuo at 75° C. to give ethyl N-(2-dimethoxyethyl)-2,6-diphenyl-4-methylpyrrole-3-carboxylate, in the form of a pale yellow, powdery solid (18.08 g).

Concentrated sulphuric acid (100 ml) was treated with a suspension of ethyl N-(2-dimethoxyethyl)-2,6-diphenyl-4-methylpyrrole-3-carboxylate (18.0 g) in glacial acetic acid (75 ml) during 10 minutes, with stirring, keeping the temperature below 50° C. by means of an ice-bath, and the mixture was stirred in the ice-bath for a further period of 20 minutes. The mixture was then poured into a mixture of crushed ice (1 liter) with a solution of sodium hydroxide (95 g) in water (1 liter), and extracted with dichloromethane (3×500 ml). The combined extract was washed with dilute aqueous sodium chloride solution, dried over a mixture of magnesium sulphate and charcoal, and evaporated in vacuo. The resulting residue was recrystallised from methanol, to give ethyl 3-methyl-1-phenylpyrrolo[2,1-a]isoquinoline-2-carboxylate (6.9 g), in the form of colourless crystals, m.p.119°-121° C.[N.M.R. (in CDCl$_3$); 0.91 (3H, t, J=7.5 Hz), 1.81 (3H, s), 4.07 (2H, q, J=7.5), 6.83 (1H, d, J=4 Hz), 7.10 (1H, dt, J=1 and 4 Hz), 7.16-7.56 (8H, m), 7.64 (1H, d, J=4 Hz)].

By proceeding in a manner similar to that described in Reference Examples 1(c) to 1(g), there were then prepared, respectively:

(b) 2-hydroxymethyl-3-methyl-1-phenylpyrrolo[2,1-a]-isoquinoline, in the form of a waxy solid;

(c) 3-methyl-1-phenylpyrrolo[2,1-a]isoquinoline-2-carboxaldehyde, in the form of a yellow solid, m.p. 174°-179° C. [N.M.R. (in CDCl$_3$): 2.84 (3H, s), 6.90 (1H, d, J=7 Hz), 7.16 (1H, dt, J=2 and 8 Hz), 7.30 (1H, dt, J=2 and 8 Hz), 7.40-7.60 (7H, m), 7.67 (1H, d, J=7 Hz), 9.79 (1H, s)];

(d) ethyl (E)-3-(3-methyl-1-phenylpyrrolo[2,1-a]-isoquinolin- 2-yl)propenoate, in the form of a bright yellow solid, m.p. 148°-152° C. [N.M.R. (in CDCl$_3$): 1.14 (3H, t, J=7 Hz), 2.63 (3H, s), 4.16 (2H, q, J=7 Hz), 5.63 (1H, d, J=16 Hz), 6.79 (1H, d, J=7 Hz), 7.10 (1H, dt, J=2 and 8 Hz), 7.18-7.65 (8H, m), 7.62 (1H, d, J=7 Hz), 7.76 (1H, d, J=16 Hz)];

(e) (E)-3-(3-methyl-1-phenylpyrrolo[2,1-a]isoquinolin-2-yl)propen-1-ol, in the form of an oil; and (f) (E)-3-(3-methyl-1-phenylpyrrolo[2,1-a]isoquinolin-2-yl)propenal, in the form of a yellow solid, m.p. 151°-155° C. [N.M.R. (in CDCl$_3$): 2.64 (3H, s), 6.01 (1H, dd, J=8 and 15 Hz), 6.82 (1H, d, J=8 Hz), 7.11 (1H, dt, J=2 and 8 Hz), 7.20-7.65 (10H, m), 7.61 (1H, d, J=8 Hz), 9.41 (1H, d, J=8 Hz)].

(g) By proceeding in a manner similar to that described in Reference Example 1(h), but using ethyl acetoacetate instead of methyl acetoacetate, there was then prepared ethyl (E)-5-hydroxy-7-(3-methyl-1-phenylpyrrolo[2,1-a]isoquinolin-2-yl)-3-oxohept-6-enoate, in the form of an oil.

REFERENCE EXAMPLE 5

(a) A mixture of methyl propionylacetate (85.7 g), 4-fluorobenzaldehyde (81.7 g), piperidine (6 ml), glacial acetic acid (15 ml) and toluene (400 ml) was stirred at reflux for 18 hours, drying by means of a Dean & Stark distillation head. The cooled mixture was diluted with diethyl ether, washed with dilute aqueous sodium chloride solution and with water, and dried over magnesium sulphate. The solution was concentrated in vacuo and the residue was distilled, to give a mixture of the syn and anti-isomers of methyl 2-(4-fluorobenzylidene)-3-oxopentanoate (114 g), in the form of a pale yellow oil, b.p. 108° C./0.15 mmHg-140° C./0.4 mmHg. [Elemental analysis: C,65.9;H,5.60;F,8.05%; calculated: C,66.1;H,5.55;F,8.04%; I R. 1727, 1705, 1672, 1625, 1601, 1263, 1233, 1231, 1196, 1162, 837cm$^{-1}$; N.M.R. (in CDCl$_3$): 0.90 and 0.96 (3H, two triplets, J=7 Hz), 2.59 and 2.76 (2H, two quartets, J=7 Hz), 3.82 and 3.85 (3H, two singlets), 7.00-7.16 (2H, m), 7.28-7.52 (2H, m), 7.57 and 7.67 (1H, two singlets)].

(b) A mixture of methyl 2-(4-fluorobenzylidene)-3-oxopentanoate (52.0 g), benzaldehyde (25.4 g), triethylamine (22 g), 3,4-dimethyl-5-(2-hydroxyethyl)-thiazolium iodide (6.3 g) and ethanol (100 ml) was heated at reflux under nitrogen for 16 hours. The cooled mixture was diluted with dichloromethane, and washed with dilute hydrochloric acid (2N), with dilute aqueous sodium bicarbonate solution, and with water, and dried over magnesium sulphate. The solution was concentrated in vacuo and the residue was dissolved in hot methanol. The resulting off-white solid was filtered off, to give methyl 2-(1-oxopropyl)-3-(4-fluorophenyl)-4-phenyl-4-oxobutanoate (21.5 g), m.p. 104°-109° C. [Elemental analysis: C,70.1;H,5.42;F,5.58%; calculated: C,70.15;H,5.60; F,5.55%; I.R. 1749, 1738, 1716, 1708, 1679, 1508, 761, 697cm$^{-1}$ [N.M.R. (in CDCl$_3$): 0.81 and 1.08 (3H, two triplets, J=7 Hz), 1.80-2.04 and 2.46-2.80 (2H, two sets of multiplets), 3.53 and 3.68 (3H, two singlets), 4.58 and 4.62 (1H, two doublets, J=10 Hz), 5.39 and 5.42 (1H, two doublets, J=10 Hz), 6.96 (2H, t, J=8 Hz), 7.20-7.60 (5H, m), 7.90-8.00 (2H, m)].

(c) A solution of aminoacetaldehyde dimethyl metal (8.55 g) and methyl 2-(1-oxopropyl)-3-(4-fluorophenyl)-4-phenyl-4-oxobutanoate (25.3 g) in glacial acetic acid (240 ml) was heated at reflux under nitrogen for 16 hours. After cooling, the solution was added, slowly with stirring, to sulphuric acid (120 ml), keeping the temperature below 15° C. by means of an ice-bath. After the addition, the solution was stirred for a further period of 30 minutes and then it was poured into water, to give a brown solid. This solid was filtered off and subjected to chromatography on a column of silica gel, using a 1:2v/v mixture of light petroleum (b.p. 60°-80° C.) and diethyl ether as eluent, to give methyl 1-(4-fluorophenyl)-3-ethylpyrrolo[2,1-a]isoquinoline-2-carboxylate (5.8 g) [N M.R. (in CDCl$_3$): 1.31 (3H, t, J=7 Hz), 3.31 (2H, q, J=7 Hz), 3.62 (3H, s), 6.82 (1H, d, J=8 Hz), 7.00-7.42 (7H, m), 7.49 (1H, dd, J=2 and 8 Hz), 7.69 (1H, d, J=8 Hz)].

By proceeding in a manner similar to that described in Reference Examples 1(c) to 1(h), there were then prepared, respectively:

(d) 2-hydroxymethyl-3-ethyl-1-(4-fluorophenyl)pyrrolo-[2,1-a]isoquinoline, in the form of a thick oil;

(e) 3-ethyl-1-(4-fluorophenyl)pyrrolo[2,1-a]isoquinoline-2-carboxaldehyde, in the form of a yellow solid;

(f) ethyl (E)-3-{3-ethyl-1-(4-fluorophenyl)pyrrolo[2,1-a]isoquinolin-2-yl}propenoate, in the form of a deep yellow solid, m.p. 142°-144° C. [N.M.R. (in CDCl$_3$): 1.25 (3H, t, J=7 Hz), 1.34 (3H, t, J=7 Hz), 3.10 (2H, q, J=7 Hz), 4.18 (2H, q, J=7 Hz), 5.62 (1H, d, J=16 Hz), 6.78 (1H, d, J=8 Hz), 7.05-7.56 (8H, m), 7.66 (1H, d, J=8 Hz), 7.71 (1H, d, J=16 Hz)];

(g) (E)-3-{3-ethyl-1-(4-fluorophenyl)pyrrolo[2,1-a]-isoquinolin-2-yl}propen-1ol, in the form of a gum; and (h) (E)-3-(3-ethyl-1-(4-fluorophenyl)pyrrolo[2,1-a]-isoquinolin-2-yl}propenal, in the form of an orange-yellow solid, [N.M.R. (in CDCl$_3$): 1.34 (3H, t, J=8 Hz), 3.14 (2H, q, J=8 Hz), 6.02 (1H, dd, J=8 and 16 Hz), 6.83 (1H, d, J=7 Hz), 7.04-7.60 (9H, m), 7.69 (1H, d, J=7 Hz), 9.43 (1H, d, J=8 Hz)].

(i) By proceeding in a manner similar to that described in Reference Example 1(h), but using ethyl acetoacetate instead of methyl acetoacetate, there was then prepared ethyl (E)-5-hydroxy-7-{3-ethyl-1-(4-fluorophenyl)pyrrolo[2,1-a]isoquinolin-2-yl}-3-oxohept-6-enoate N.M.R. (in CDCl$_3$): 1.20-1.35 (6H, m), 2.70 (2H, m), 3.04 (2H, q, J=7 Hz), 3.47 (2H, s), 4.22

(2H, q, J=7 Hz), 4.59 (1H, q, J=6 Hz), 5.44 (1H, dd, J=6 and 16 Hz), 6.52 (1H, dd, J=2 and 16 Hz), 6.75 (1H, d, J=8 Hz), 7.00–7.45 (7H, m), 7.49 (1H, dd, J=1 and 7 Hz), 7.67 (1H, d, J=8 Hz)].

REFERENCE EXAMPLE 6

(a) By proceeding in a manner similar to that described hereinbefore in Reference Example 1(a), but replacing the 1-cyano-2-isobutyryl-1,2-dihydroisoquinoline, used as starting material, by the appropriate quantity of 1-cyano-2-(4-fluorobenzoyl)-1,2-dihydroisoquinoline, there was prepared 1-amino-3-(4-fluorophenyl)oxazolo-[4,3-a]isoquinolinium tetrafluoroborate, in the form of a Yellow solid, m.p. 198°–200° C. (with decomposition) [Elemental analysis: C,55.8;H,3.35;N,7.6%; calculated: C,55.8;H,3.3;N,7.7%].

(b) By then proceeding in a manner similar to that described hereinbefore in Reference Example 1(b), but replacing the ethyl phenylpropiolate, used as a starting material, by the appropriate quantity of methyl 4-methylpent-2-ynoate, and using 1,3-dimethylimidazolin-2-one as a solvent, there was prepared methyl 3-(4-fluorophenyl)-1-isopropylpyrrolo[2,1-a]isoquinoline-2-carboxylate in the form of a colourless solid, m.p. 114°–115° C. [Elemental analysis: C,76.1;H,5.53;N.3.8%; calculated: C,76.5;H,5.54;N.3.9%; [N.M.R. (in CDCl3) 1.55 (6H, d, J=7 Hz), 3.69 (3H, s), 4.01 (1H, septet, J=7 Hz), 6.63 (1H, d, J=8 Hz), 7.12–7.56 (8H, m), 8.25 (1H, d, J=8 Hz); Mass spectrum (electron impact) m/e=361].

By proceeding in a manner similar to that described in Reference Examples 1(c) to 1(h), there were then prepared, respectively:

(c) 2-hydroxymethyl-1-isopropyl-3-(4-fluorophenyl)-pyrrolo[2,1-a]isoquinoline, in the form of a colourless solid, m.p. 121°–123° C. [N.M.R. (in CDCl3 and D2O): 1.62 (6H, d, J=7 Hz), 4.03 (1H, septet, J=7 Hz), 4.71 (2H, s), 6.60 (1H, d, J=8 Hz), 7.16–7.60 (8H, m), 8.25 (1H, d, J=8 Hz); Mass spectrum (electron impact) m/e=333];

(d) 1-isopropyl-3-(4-fluorophenyl)pyrrolo[2,1-a]-isoquinoline-2-carboxaldehyde, in the form of a yellow solid, m.p. 175°–178° C.: [N.M.R. (in CDCl3): 1.60 (6H, d, J=7 Hz), 4.18 (1H, septet, J=7 Hz), 6.69 (1H, d, J=8 Hz), 7.11–7.58 (8H, m), 8.32 (1H, d, J=8 Hz), 9.92 (1H, s); Mass spectrum (electron impact) m/e=331];

(e) ethyl (E)-3-{1-isopropyl-3-(4-fluorophenyl)pyrrolo[2,1-a]isoquinolin-2-yl}propenoate, in the form of a pale yellow solid, m.p. 186°–188° C. [N.M.R. (in CDCl3): 1.26 (3H, t, J=7 Hz),1.58 (6H, d, J=7 Hz), 4.06 (1H, septet, J=7 Hz), 4.17 (2H, d, J=7 Hz), 5.55 (1H, d, J= 16 Hz), 6.59 (1H, d, J=8 Hz), 7.18–7.53 (8H, m), 8.05 (1H, d, J=16 Hz), 8.25 (1H, d, J=8 Hz)]; Mass spectrum (electron impact) m/e=401];

(f) (E)-3-{1-isopropyl3-(4fluorophenyl)pyrrolo-[2,1-a]isoquinolin-2-yl}propen-1-ol, in the form of a Yellow viscous oil [N.M.R. (in CDCl3): 1.55 (6H, d, J=7 Hz), 4.01 (1 H, septet, J=7 Hz), 4.11 (2H, dd, J=1Hz and 6 Hz), 5.49 (1H, d, t, J=6 and 16 Hz), 6.54 (1H, d, J=8 Hz), 6.80 (1H, d, t, J=1 and 16 Hz), 7.1–7.51 (8H, m), 8.23 (1H, d, J=8 Hz)];

(g) (E-3-{1-isopropyl-3-(4-fluorophenyl)pyrrolo-[2,1-a]isoquinolin-2-yl}propenal, in the form of a yellow solid, m.p. 157°–160° C. [N.M.R. (in CDCl3): 1.62 (6H, d, J=7 Hz), 4.13 (1H, septet, J=7 Hz), 5.92 (1H, dd, J=8 and 16 Hz), 6.64 (1H, d, J. 8 Hz), 7.2–7.57 (8H, m), 7.86 (1H, d, J=16 Hz), 8.27 (1H, d, J=8 Hz), 9.48 (1H, d, J=8 Hz)].

(h) By proceeding in a manner similar to that described in Reference Example 1(h), but using ethyl acetoacetate instead of methyl acetoacetate, there was then prepared ethyl (E)-5-hydroxy-7-{1-isopropyl-3-(4-fluorophenyl)pyrrolo[2,1-a]isoquinolin-2-yl}-3-oxohept- 6-enoate in the form of a viscous orange oil [N.M.R. (in CDCl3): 1.28 (3H, t, J=7 Hz), 1.54 (6H, d, J=7 Hz), 2.58–2.63 (2H, m), 3.43 (2H, s), 4.01 (1H, septet, J=7 Hz), 4.22 (2H, q, J=7 Hz), 4.61 (1H, m), 5.28 (1H, dd, J=7 and 16 Hz), 6.55 (1H, d, J=8 Hz), 6.85 (1H, dd, J=1 and 16 Hz), 7.14–7.52 (8H, m), 8.24 (1H, d, J=8 Hz)].

REFERENCE EXAMPLE 7

(a) By proceeding in a manner similar to that described hereinbefore in Reference Example 1(b), but replacing the ethyl phenylpropiolate, used as a starting material, by the appropriate quantity of methyl 4-fluorophenylpropiolate, there was prepared methyl 1-(4-fluorophenyl)-3-isopropylpyrrolo[2,1-a]isoquinoline-2-carboxylate in the form of a colourless solid, m.p. calculated: C,76.5;H,5.54;N.3.9%; [N.M.R. (in CDCl3): 1.51 (6H, d, J=7 Hz), 3.58 (3H, s), 4.11 (1H, septet, J=7 Hz), 6.76 (1H, d, J=8 Hz), 7.03–7.52 (8H, m), 7.84 (1H, d, J=8 Hz); Mass spectrum (electron impact) m/e=361]. By proceeding in a manner similar to that described in Reference Examples 1(c) to 1(h), there were then prepared, respectively:

(b) 2-hydroxymethyl-3-isopropyl-1-(4-fluorophenyl)-pyrrolo[2,1-a]isoquinoline, in the form of a pale yellow gum [N.M.R. (in CDCl3 and D2O): 1.52 (6H, d, J=7 Hz), 3.58 (1H, septet, J=7 Hz), 4.54 (2H, s), 6.71 (1H, d, J=8 Hz), 7.02–7.50 (8H, m), 7.79 (1H, d, J=8 Hz)];

(c) 3-isopropyl-1-(4-fluorophenyl)pyrrolo[2,1-a]-isoquinoline-2-carboxaldehyde, in the form of a pale yellow solid, m.p. 145°–146° C.; [Elemental analysis: C,79.8;H,5.6;N,4.3%; calculated: C,79.7;H,5.5;N,4.2%; N.M.R. (in CDCl3): 1.53 (6H, D, J=7 Hz), 4.16 (1H, septet, J=7 Hz), 6.82 (1H, d, J=8 Hz), 7.08–7.53 (8H, m), 7.87 (1H, d, J=8 Hz), 9.78 (1H, s); Mass spectrum (electron impact) m/e=331];

(d) ethyl (E)-3-{3-isopropyl-1-(4-fluorophenyl)pyrrolo[2,1-a]isoquinolin-2-yl)propenoate, in the form of a pale yellow solid, m.p. 151°–153° C. [Elemental analysis: C,77.5;H,6.25;N,3.3%; calculated: C,77.8;H,6.03;N,3.5%; N.M.R. (in CDCl3) 1.16 (3H, t, J=7 Hz), 1.56 (6H, d, J=7 Hz), 3.67 (1H, septet, J=7 Hz), 4.17 (2H, d, J=7 Hz), 5.42 (1H, d, J=16 Hz), 6.72 (1H, d, J=8 Hz), 7.03–7.52 (8H, m), 7.844 (1H, d, J=8 Hz), 7.87 (1H, d, J=16 Hz); Mass spectrum (electron impact) m/e=401];

(e) (E)-3-{3-isopropyl-1-(4-fluorophenyl)pyrrolo2,1-a]isoquinolin-2-yl}propen-1-ol, in the form of a yellow oil [N.M.R. (in CDCl3 and D2O): 1.51 (6H, d, J=7 Hz), 3.67 (1 H, septet, J=7 Hz), 4.1 (2H, dd, J=1Hz and 6 Hz), 5.48 (1H, d, t, J=6 and 16 Hz), 6.58 (1H, d, t, J=1 and 16 Hz), 6.69 (1H, d, J=8 Hz), 7.02–7.50 (8H, m), 7.83 (1H, d, J=8 Hz); Mass spectrum (electron impact) m/e=359];

(f) (E)-3-{3-isopropyl-1-(4-fluorophenyl)pyrrolo-2,1-a]isoquinolin-2-yl}propenal, in the form of a yellow solid, m.p. 155°–157° C. [Elemental analysis: C,80.5; H,5.72;N,3.9%; calculated: C,80.6;H,5.64;N,3.9%; N.M.R. (in CDCl3): 1.60 (6H, d, J=7 Hz), 3.78 (1H, septet, J=7 Hz), 5.78 (1H, dd, J=8 and 16 Hz), 6.77 (1H, d, J=8 Hz), 7.05–7.54 (8H, m), 7.62 (1H, d, J=16

Hz), 7.84 (1H, d, J=8 Hz), 9.41 (1H, d, J=8 Hz); Mass spectrum (electron impact) m/e=357].

(g) By proceeding in a manner similar to that described in Reference Example 1(h), but using ethyl acetoacetate instead of methyl acetoacetate, there was then prepared ethyl (E)-5-hydroxy-7-{3-isopropyl-1-(4-fluorophenyl)pyrrolo[2,1-a]isoquinolin-2-yl}-3-oxohept6-enoate in the form of a pale yellow gum [N.M.R. (in CDCl$_3$ and D$_2$O): 1.26 (3H, t, J=7 Hz), 1.49 (6H, d, J=7 Hz), 2.56–2.64 (2H, m), 3.43 (2H, s), 3.62 (1H, septet, J=7 Hz), 4.20 (2H, q, J=7 Hz), 4.48–4.6 (1H, m), 5.22 (1H, dd, J=7 and 16 Hz), 6.63 (1H, d, J=16 z), 6.69 (1H, d, J=8 Hz), 7.01–7.50 (8H, m), 7.81 (1H, d, J=8 Hz)].

REFERENCE EXAMPLE 8

(a) A stirred solution of methyl 2-phenyl-2-bromoacetate (53.8 g) in acetonitrile (450 ml) was treated with triethylamine (45.2 ml). The mixture was then cooled in an ice-bath and treated, dropwise during 15 minutes, with a solution of aminoacetaldehyde dimethylacetal (37.8 ml) in acetonitrile (80 ml), keeping the temperature below 45° C. The mixture was stirred at room temperature for 2 hours and then left to stand for 48 hours. The mixture was then diluted with diethyl ether (800 ml) and washed with water (3×250 ml). The ethereal was dried over magnesium sulphate and evaporated, to give methyl 2-(2,2-dimethoxyethylamino)phenylacetate (55.5 g), in the form of a colourless oil [N.M.R. (in CDCl$_3$) 2.10 (1H, b), 2.57–2.79 (2H, m), 3.34 (3H, s), 3.37 (3H, s), 3.68 (3H, s), 4.50 (1H, t, J=6 Hz), 7.35 (5H, m)].

(b) A solution of methyl 2-(2,2-dimethoxyethylamino)phenylacetate (55.0 g) and triethylamine (36.5 ml) in dichlormethane (450 ml) was treated with a solution of isobutyryl chloride (25 ml) in dichloromethane (150 ml), at such a rate as to maintain gentle reflux. The pink mixture was stirred at room temperature for 2 hours and then it was washed with water (250 ml), dilute hydrochloric acid (0.5N; 300 ml), water (250 ml), aqueous sodium hydroxide solution (0.5N; 300 ml) and then with water (2×250 ml), dried over magnesium sulphate, and evaporated, to give methyl 2-phenyl-2-[N-(2,2-dimethoxyethyl)-2-methylpropanamido]acetate in the form of a pale red oil [N.M.R. (in CDCl$_3$): 1.14 (6H, d, J=7 Hz), 3.10–3.30 (7H, m), 3.36–3.44 (2H, m), 3.54 (1H, t, J=6 Hz), 3.75 (3H, s), 6.07 (1H, s), 7.22–7.46 (5H, m)].

(c) A solution of methyl 2-phenyl-2-[N-(2,2-dimethoxyethyl)-2-methylpropanamido]acetate (72.3 g) in methanol (800 ml) was treated with a solution of sodium hydroxide (30 g) in water (200 ml). The mixture was stirred for 2.5 hours and then left to stand at room temperature for 18 hours. It was then concentrated to 500 ml and diluted with water (500 ml), washed with diethyl ether (2×200 ml), cooled to below 10° C., and acidified by treatment with hydrochloric acid (4N), maintaining the temperature below 10° C. The precipitated product was extracted with ethyl acetate (3×750 ml) and the combined extracts were washed with brine (300 ml) and evaporated, to give an off-white solid, which was recrystallised from a mixture of ethanol and ethyl acetate and washed with light petroleum, to give 2-phenyl-2-[N-(2,2-dimethoxyethyl)-2-methylpropanamido]acetic acid (67.2 g), in the form of a white solid, m.p. 147°–149° C. [Elemental analysis: C,62.3;H,7.6;N,4.54%; calculated: C,62.1; H,7.4;N,4.53%].

(d) A suspension of 2-phenyl-2-[N-(2,2-dimethoxyethyl)-2-methylpropanamido]acetic acid (32.1 g) and methyl 4-fluorophenylpropiolate (22.5 g) in acetic anhydride (120 ml) was treated with triethylamine (16 ml) and the resulting amber solution was stirred at room temperature under argon for 24 hours. The solution was then added, dropwise during 10 minutes, to concentrated sulphuric acid (200 ml), stirring and cooling by means of an icebath. The mixture was stirred for 30 minutes and then it was poured into iced water (2.5 liters), and extracted with dichloromethane (3×400 ml). The combined extracts were washed with water (250 ml) and with brine (250 ml), dried over magnesium sulphate and evaporated, to give a brown solid, which was recrystallised from methanol, to give methyl 1-(4-fluorophenyl)-3-isopropylpyrrolo[2,1-a]isoquinoline-2-carboxylate in the form of an off-white solid, m.p. 170°–173° C.

The present invention includes within its scope pharmaceutical compositions which comprise at least one of the compounds of formula I or a pharmaceutically acceptable salt thereof in association with a pharmaceutically acceptable carrier or coating. In clinical practice the compounds of the present invention may be administered parenterally, but are preferably administered rectally or, more preferably, orally.

Solid compositions for oral administration include compressed tablets, pills, powders and granules. In such solid compositions, one or more of the active compounds is, or are, admixed with at least one inert diluent such as starch, sucrose or lactose. The compositions may also comprise, as is normal practice, additional substances other than inert diluents, e.g. lubricating agents, such as magnesium stearate.

Liquid compositions for oral administration include pharmaceutically acceptable emulsions, solutions, suspensions, syrups and elixirs containing inert diluents commonly used in the art such as water and liquid paraffin. Besides inert diluents such compositions may comprise adjuvants, such as wetting and suspending agents, and sweetening, flavouring, perfuming and preserving agents. The compositions according to the invention for oral administration also include capsules of absorbable material such as gelatin, containing one or more of the active substances with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. The compositions may also contain adjuvants such as stabilising, preserving, wetting, emulsifying and dispersing agents. They may be sterilised, for example, by filtration through a bacteria-retaining filter, by incorporation in the compositions of sterilising agents, by irradiation or by heating. They may also be manufactured in the form of sterile solid compositions, which can be dissolved in sterile water or some other sterile injectable medium immediately before use.

Solid compositions for rectal administration include suppositories formulated in accordance with known methods and containing one or more of the compounds of formula I or a pharmaceutically acceptable salt thereof.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally between 0.1 and 50, preferably 0.5–5, mg/kg body weight per day by oral administration.

The following Example illustrates pharmaceutical compositions according to the present invention.

Composition Example 1

No. 2 size gelatin capsules each containing:

| | |
|---|---|
| 2:1 mixture of erythro- and threo-diastereoisomers of sodium (E)-3,5-dihydroxy-7-(3-isopropyl-1-phenylpyrrolo[2,1-a]-isoquinolin-2-yl)hept-6-enoate | 20 mg |
| lactose | 100 mg |
| starch | 60 mg |
| dextrin | 40 mg |
| magnesium stearate | 1 mg | were prepared in accordance with the usual procedure.

The active ingredient may be replaced by the appropriate quantity of any other of the compounds of formula I.

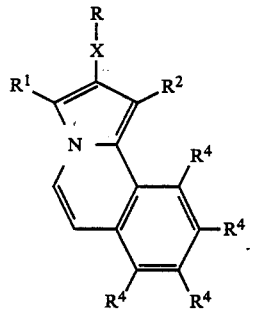

I

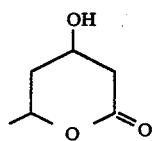

III

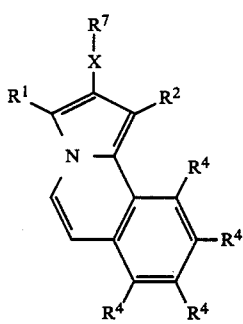

IV

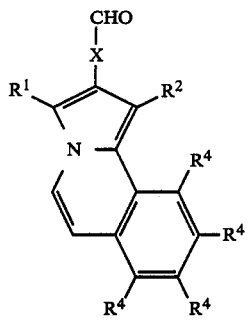

VI

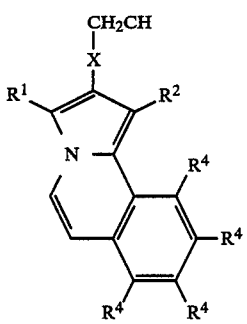

VIII

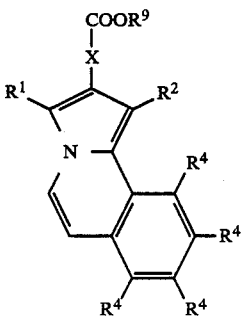

IX

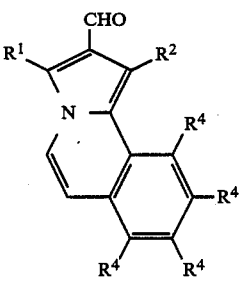

X

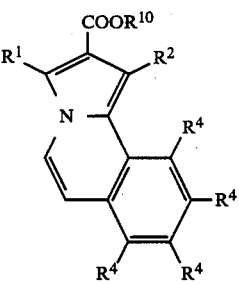

XI

-continued

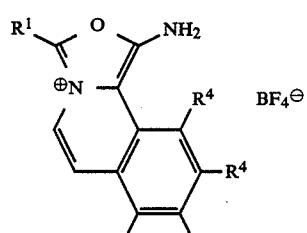 XII

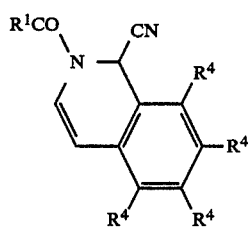 XIV

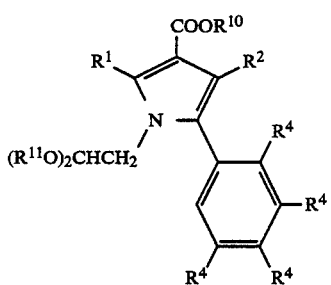 XV

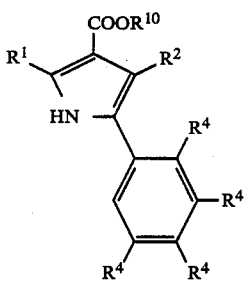 XVI

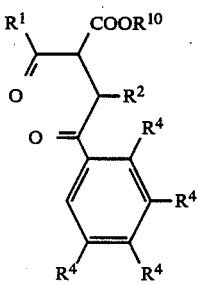 XVIII

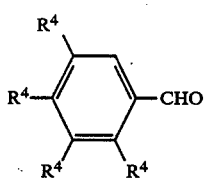 XX

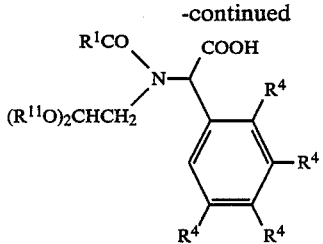 XXIII

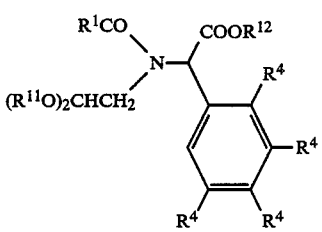 XXIV

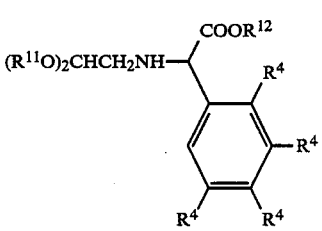 XXV

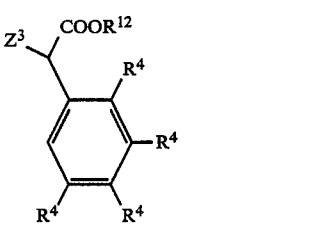 XXVII

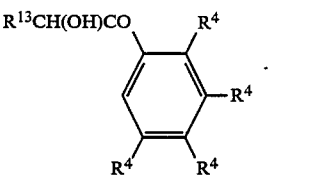 XXVIII

We claim:
1. A pyrrolo[2,1-a]isoquinoline derivative of the formula

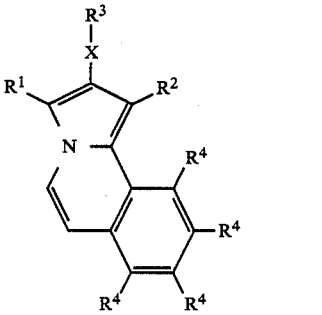

wherein $R^1$ and $R^2$, which may be the same or different, each represent a cycloalkyl group containing from 3 to 8 carbon atoms, or represent a straight- or branched-chain alkyl, alkenyl or alkynyl group containing up to 6 carbon atoms, which may be substituted by up to 3 halogen atoms, or a phenyl group unsubstituted or substituted by one or more substituents selected from halogen atoms, cycloalkyl and cycloalkenyl groups each containing from 4 to 8 carbon atoms, straight- or branched-chain alkyl, alkenyl or alkynyl groups each containing up to 6 carbon atoms and unsubstituted or substituted by up to 3 substituents selected from halogen atoms and straight- or branched-chain alkoxy and alkylthio groups each containing up to 6 carbon atoms, hydroxy groups, straight- or branched-chain alkoxy, alkylthio, alkylsulphinyl, alkylsulphonyl, alkoxycarbonyl and alkanoyl groups each containing up to 6 carbon atoms and phenyl groups unsubstituted or substituted by one or more substituents on phenyl as hereinbefore defined, X represents an ethylene or vinylene group, $R^3$ represents a group of the formula:

wherein Y represents a carbonyl or hydroxymethylene group and $R^5$ represents a hydrogen atom or an alkyl group containing up to 6 carbon atoms unsubstituted or substituted by up to 3 substituents selected from halogen atoms and straight- or branched-chain alkoxy and alkylthio groups each containing up to 6 carbon atoms, or $R^3$ represents a lactone ring of the formula:

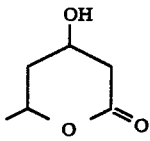

and the symbols $R^4$ may be the same or different and each represents a hydrogen or halogen atom or represents a straight- or branched-chain alkyl, alkenyl or alkynyl group containing up to 6 carbon atoms and unsubstituted or substituted by up to 3 substituents selected from halogen atoms and straight- or branched-chain alkoxy and alkylthio groups each containing up to 6 carbon atoms, or a phenyl group unsubstituted or substituted by one or more substituents selected from halogen atoms, cycloalkyl and cycloalkenyl groups each containing from 4 to 8 carbon atoms, straight- or branched-chain alkyl, alkenyl or alkynyl groups each containing up to 6 carbon atoms and unsubstituted or substituted by up to 3 substituents selected from halogen atoms and straight- or branched-chain alkoxy and alkylthio groups each containing up to 6 carbon atoms, hydroxy groups, straight- or branched-chain alkoxy, alkylthio, alkylsulphinyl, alkylsulphonyl, alkoxycarbonyl and alkanoyl groups each containing up to 6 carbon atoms and phenyl groups unsubstituted or substituted by one or more substituents on phenyl as hereinbefore defined, or a group of the formula $R^6O-$, wherein $R^6$ represents a straight or branched-chain alkyl group containing up to 6 carbon atoms, a phenyl group, or a benzyl or phenethyl group or a pharmaceutically acceptable salt thereof when $R^5$ represents a hydrogen atom.

2. A compound according to claim 1 wherein $R^1$ and $R^2$ are different, and X represents a vinylene group in the E configuration.

3. A compound according to claim 1 wherein one of $R^1$ and $R^2$ represents an unsubstituted or substituted phenyl group and the other represents a cycloalkyl group containing from 3 to 8 carbon atoms, or a straight- or branched-chain alkyl, alkenyl or alkynyl group containing up to 6 carbon atoms, which may be substituted by up to 3 halogen atoms.

4. A compound according to claim 3 wherein $R^2$ represents a substituted or unsubstituted phenyl group.

5. A compound according to claim 3 wherein $R^2$ represents a phenyl group substituted by a halogen atom in 4-position.

6. A compound according to claim 3, wherein $R^1$ represents a straight- or branched-chain alkyl group.

7. A compound according to claim 1 wherein Y represents a hydroxymethylene group.

8. A compound according to claim 1 wherein $R^5$ represents a hydrogen atom or a methyl or ethyl group.

9. A compound according to claim 1 wherein the symbols $R^4$ all represent hydrogen atoms.

10. A compound according to claim 1 wherein $R^3$ represents a group of formula II, Y represents a hydroxymethylene group, and the compound is in the erythro form.

11. A compound according to claim 1 which is methyl, ethyl or sodium (E)-3,5-dihydroxy-7-(3-isopropyl-1-phenylpyrrolo[2,1-a]isoquinolin-2-yl)hept-6-enoate; ethyl (E)-3-hydroxy-7-(3-isopropyl-1-phenylpyrrolo-[2,1-a]-isoquinolin-2-yl)-5-oxohept-6-enoate; (E)-3-hydroxy-7-(3-isopropyl-1-phenylpyrrolo[2,1-a]isoquinolin-2-yl)-5-oxohept-6-enoic acid; 3,5-dihydroxy-7-(3-isopropyl-1-phenylpyrrolo-[2,1-a]isoquinolin-2-yl)heptanoic acid; ethyl or sodium (E)-3,5-dihydroxy-7-(3-methyl-1-phenylpyrrolo[2,-1-a]isoquinolin-2-yl)hept-6-enoate; ethyl or sodium (E)-3,5-dihydroxy-7-{3-ethyl-1-(4-fluorophenyl)pyrrolo-[2,1-a]isoquinolin-2-yl}hept-6-enoate; ethyl or sodium (E)-3,5-dihydroxy-7-{1-isopropyl-3-(4-fluorophenyl)pyrrolo-2,1-a]isoquinolin-2-yl}-hept-6-enoate; ethyl or sodium (E)-3,5-dihydroxy-7-{3-isopropyl-1-(4-fluorophenyl)pyrrolo-2,1-a]isoquinolin-2-yl}-hept-6-enoate; ethyl or sodium (E)-3-hydroxy-7-{3-isopropyl-1-(4-fluorophenyl)-pyrrolo[2,1-a]-isoquinolin-2-yl]-5-oxohept-6-enoate; or the threo or erythro forms of the foregoing 3,5-dihydroxy compounds or a mixture of the threo and erythro forms; or 4-hydroxy-6-[2-(3-isopropyl-1-phenyl-pyrrolo-[2,1-a]isoquinolin-2-yl)ethyl-3,4,5,6-tetrahydro-2H-pyran-2-one; or the cis- or trans- lactone ring isomers thereof or a mixture thereof.

12. A pharmaceutical composition useful in the prevention or treatment of hypercholesterolaemic and hyperlipoproteinaemic states, of atherosclerosis and of associated conditions which comprises an effective amount of a pyrrolo[2,1-a]isoquinoline derivative according to claim 1, or a pharmaceutically acceptable salt thereof, in association with a pharmaceutically acceptable diluent or carrier.

* * * * *